United States Patent [19]

Cordon-Cardo et al.

[11] Patent Number: 5,168,043
[45] Date of Patent: Dec. 1, 1992

[54] BLOOD GROUP ANTIGEN PANEL

[75] Inventors: Carlos Cordon-Cardo, New York; Kenneth O. Lloyd, Bronx; Connie L. Finstad; Lloyd J. Old, both of New York; Mryon R. Melamed, Dobbs Ferry; Joel Sheinfeld, New York, all of N.Y.

[73] Assignee: Sloan-Kettering Institute for Cancer Research, New York, N.Y.

[21] Appl. No.: 330,591

[22] Filed: Mar. 28, 1989

Related U.S. Application Data

[63] Continuation-in-part of Ser. No. 817,874, Jan. 10, 1986, abandoned.

[51] Int. Cl.$^5$ .................. G01N 33/574; G01N 33/571
[52] U.S. Cl. ..................... 435/7.23; 435/7.1; 435/960; 436/501; 436/548; 436/63; 436/811; 436/813; 436/510
[58] Field of Search ............ 435/7.1, 7.23, 172.2, 435/240.27, 810, 960, 975; 436/501, 536, 548, 63, 808, 811, 813; 530/387, 395, 828, 829; 935/106, 110; 424/11

[56] References Cited

U.S. PATENT DOCUMENTS

4,579,827 4/1986 Sakamoto et al. ................. 436/536
4,678,747 7/1987 Lloyd et al. ............................ 435/7

OTHER PUBLICATIONS

Sakamoto, J., et al., *Molecular Immunology*, vol. 21, No. 11, pp. 1093-1098 (1984).
*Basic & Clinical Immunology*, Stites et al., eds, Lange Medical Publications, Los Altos, CA, USA pp. 387-388 (1982).
Ueda, R., et al., Proc. Natl. Acad. Sci. USA, vol. 78, 1981, pp. 5122-5126.
Rettig, Wolfgang J., et al., Cancer Research, vol. 46, 1985, pp. 815-820.
Sakamoto, Junichi, et al., Biological Abstracts, vol. 79(10), Abstract No. 86505, 1984.
Cordon-Cardo, Carlos, et al., Biological Abstracts, vol. 83(3) Abstract No. 24317, 1986.
Motzer, Robert J., et al., Biological Abstracts, vol. 86(10), Abstract No. 104687, 1988.
Cordon-Cardo, Carlos, et al., Biological Abstracts, vol. 86(7), Abstract No. 71635, 1988.
Issitt, Peter D., et al., Applied Blood Group Serology, Second Edition, 1977, Spectra Biologicals, pp. 91-92.

Primary Examiner—Esther L. Kepplinger
Assistant Examiner—Toni R. Scheiner
Attorney, Agent, or Firm—John P. White

[57] ABSTRACT

The subject invention describes a method of determining the secretor status of an individual which comprises obtaining a sample of a biological fluid from the individual and determining whether the sample includes the Lewis$^a$ or Lewis$^b$ antigens, the presence of the Lewis$^a$ antigen in the sample indicating that the individual is a nonsecretor, the presence of the Lewis$^b$ antigen in the sample indicating that the individual is a secretor, and the presence of neither antigen indicating the secretor status of the individual is inconclusive. The invention also provides a method of further determining the secretor status of an individual of having an inconclusive secretor status which comprises determining whether the biological fluid sample from the individual includes A, B or precursor type 1 chain antigens, the presence of any such antigens in the sample indicating that the individual is a secretor, the lack of any such antigens in the sample indicating that the individual is a nonsecretor. The invention provides a method of determining whether a human female subject is susceptible to urogenital infection which comprises determining whether the subject is a secretor according to the hereinabove-described methods, a secretor being susceptible to such an infection. The present application also provides a method of distinguishing urothelial carcinoma from normal tissue, and identifying human germ cell tumor as seminoma or nonseminoma. Finally, the invention provides a panel comprising some or all of the monoclonal antibodies H 29-36 (ATCC No. HB 8248), S8 (ATCC No. HB 9036), T 174 (ATCC No. HB 8242), T 218 (ATCC No. HB 8249), P 12 (ATCC No. HB 8551), F 3 (ATCC No. HB 8217), and K 21 (ATCC No. HB 8549).

14 Claims, 12 Drawing Sheets

Figure 5A  Figure 5B  Figure 5C
Figure 5D  Figure 5E  Figure 5F
  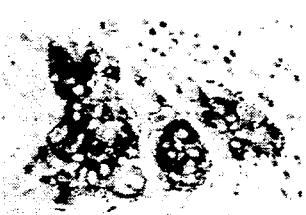
Figure 5G  Figure 5H  Figure 5I
 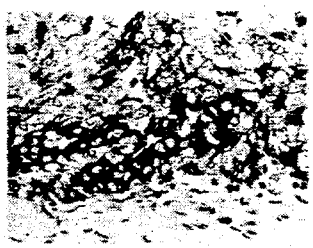
Figure 5J  Figure 5K  Figure 5L
  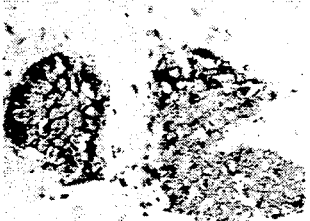

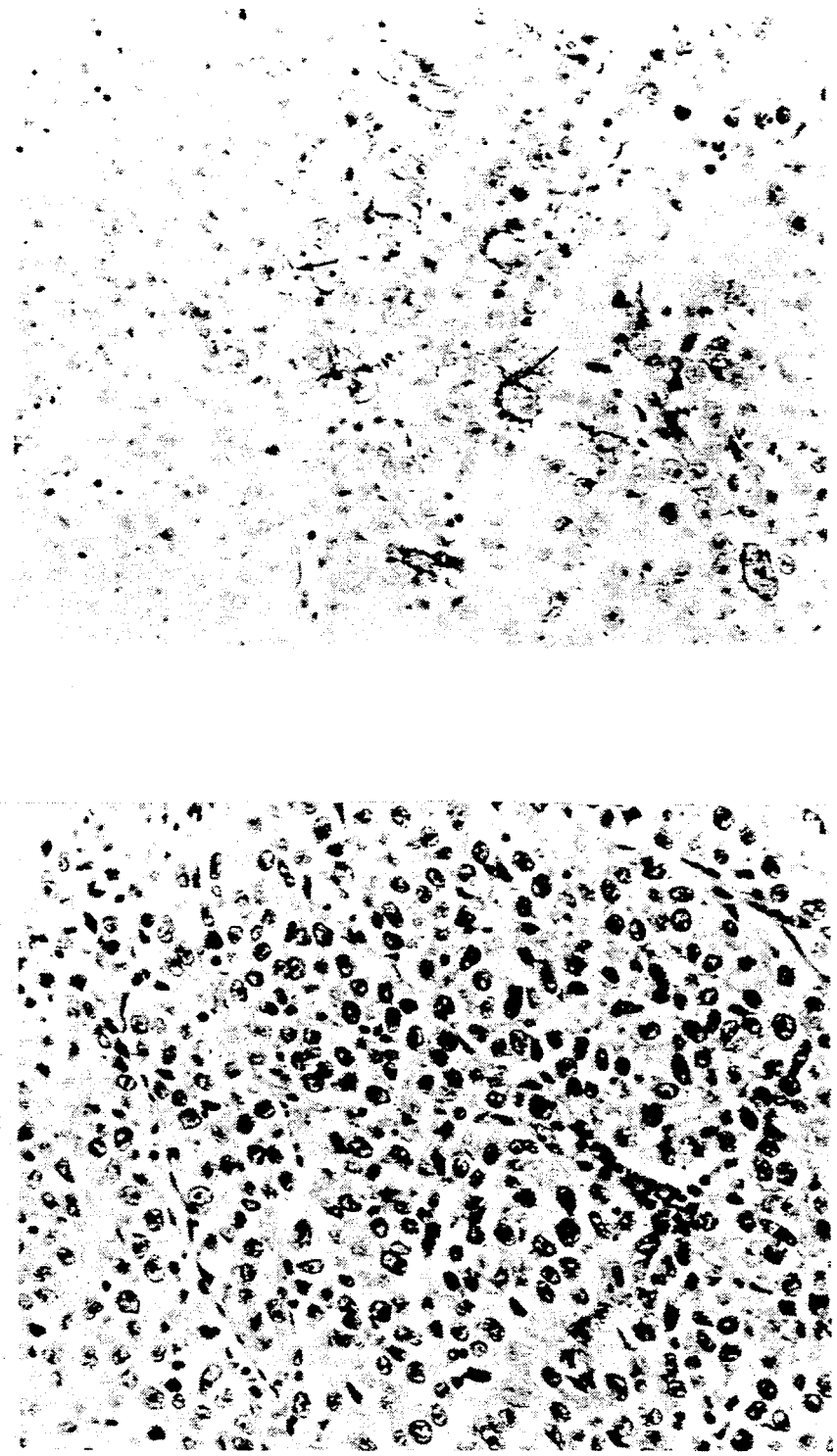

BLOOD GROUP ANTIGEN PANEL

The present invention was partially funded by the National Cancer Institute under Grants Nos. CA-41021, CA-14134, CA-21445, CA-47538, and CA-08478, Department of Health and Human Services, and by National Institute of Allergy and Infectious Diseases' Grant No. AI-16014. Accordingly, the United States Government has certain rights in this invention.

This application is a continuation-in-part of U.S. Ser. No. 817,874, filed Jan. 10, 1988, now abandoned, the contents of which are hereby incorporated by reference into the present application.

BACKGROUND OF THE INVENTION

This invention relates to the use of monoclonal antibodies in determining the presence of particular antigens. Applications of this invention include, but are not limited to, diagnosis of disease, including cancer cell typing or classification and identification of precancerous lesions.

PRIOR ART

Blood group antigens are carbohydrate determinants which are typically found on erythrocytes, certain epithelial tissues, and in body secretions. They are formed by the sequential additional of saccharides to carbohydrate side chains of lipids and proteins. Hakomori, *Seminars in Hematology* 18:39 (1981). Genes control synthesis of these structures, as well as their expression in secretions, and on cell types other than erythrocytes (red blood cells).

The "A", "B" and "H" blood group antigens are known, at least indirectly, as identifying blood "type". Presence of "H" antigen only is characteristic of "Type O" blood, whereas presence of antigen "A" and "B" in the same sample is characteristic of, respectively, type A or type B blood. Lewis antigens, i.e., $Le^a$ and $Le^b$, are typically found in plasma, secretions, and secretory epithelia.

These antigens are characteristics of other conditions, and determination of their presence is useful in areas other than blood typing. For example, Emmott, et al., *J. Urol.* 121:37 (1979) have found that the antigens of the ABH system which are usually present in normal urinary bladder tissue, are absent in urinary bladder tumors. Additional studies have shown that loss of these antigens is an early event in malignant transformation. Liss, et al., *Am. J. Clin. Pathol.* 68:372 (1977) (larynx carcinoma); Weinstein, et al., *Cancer* 43:661 (1979) (urinary bladder carcinoma). In patients with epithelial cancers, especially colon carcinomas, elevated levels of $Le^a$ and $Le^b$ antigens have been found. Koprowski, et al., *Science* 212:53 (1981). Additionally, the presence of normally incompatible blood groups in the same patient has been described in some cancer patients. Hatton, et al., *Biochem. Biophys. Acta* 666:361 (1981).

Determination of a change in the amount of blood group antigen, a sudden appearance, or disappearance, is indicative of a pathological state. Hatton, et al., supra, for example, found A antigen in type O cancer patients. Emmol, Liss, and Koprowski, supra, have all shown that disappearance or appearance of antigens is typical of cancer. Hence, it is desirable to have a method for determining the presence of blood group antigens.

Several monoclonal antibodies, which are known to be specific for blood group antigens have been used to form a "panel" for determining particular antigens. H29-36 monoclonal antibody, for example, determines the presence of all varieties of A antigen. See, e.g., Sakamoto, et al., (unpublished manuscript), copending U.S. patent application Ser. No. 474,415, "Monoclonal antibody S8 is known to detect B-antigen," Ueda, et al., *PNAS* 78:5122 (1981). Additionally, monoclonal antibodies T-174, T-218, P-12, and F-3 are specific for $Le^a$, $Le^b$, X, and Y antigens, respectively. Antibody K-21 detects precursor type antigen. Rettig, et al., *Cancer Res.* 45:815 (1985), Lloyd, et al., *Immunogenetics* 17:537 (1983).

These monoclonal antibodies all of which are described more fully, infra, are used as part of a panel to determine blood group antigens.

Blood group antigens are a group of carbohydrate determinants found on erythrocytes and certain epithelial tissues, including urothelium. The Lewis antigens, $Le^a$ and $Le^b$, are structures biochemically related to the ABO blood group. The sequential addition of saccharide residues by gene-specific glycosyltransferases to carbohydrate precursor structures confer on the cell its antigenic specificity. The ABO and Lewis antigenic profile of uroepithelial cells is the result of complex interaction between three structural gene loci: ABO, Lele and Hh. A fourth regulatory gene, the dimorphic secretor gene, (Sese), controls the H gene or its product and has recently been shown to influence the expression of the H and $Le^b$ determinants in the urothelium of all individuals, as well as the expression of A and B determinants in A, B and AB individuals. In addition to influencing the phenotypic expression of A, B, H and Lewis blood group specificities in urothelium, the secretor gene also controls the expression of these antigens in secretions such as saliva. Secretor individuals have A, B or H and $Le^b$ antigens in their secretions and have Le(a−b+) erythrocytes. Nonsecretor individuals do not secrete A, B, or H antigens, and have Le(a+b−) erythrocytes and $Le^a$ antigens in their secretions. Lewis blood typing can thus classify most individuals according to secretor status; Le(a−b+) are "secretors" and Le(a+b−) are "nonsecretors." Lewis antigens are not synthesized by erythroblasts but can be adsorbed from the plasma onto the erythrocytes, and this phenomenon may account, in part, for apparent phenotypic inconsistencies between erythrocytes and epithelia, particularly in nonsecretor individuals. The presence or absence of A, B, H, $Le^a$ and $Le^b$ on the urothelial cell surface may influence an individual's susceptibility to recurrent urinary tract infections either by providing a specific receptor site or shielding an exposed one.

Women with recurrent urinary tract infections demonstrate increased adherence of bacteria to uroepithelial, vaginal and buccal epithelial cells, when compared to females who have never had an infection. This increased adherence persists despite resolution of the infection. Furthermore, there appears to be a direct association between the bacterial receptivity of buccal cells and vaginal epithelial cells obtained from the same female and tested with the same strain of *E. coli*. This suggests that a widespread, genetically determined alteration in the cell surface composition of mucosal epithelial cells results in enhanced bacterial attachment, thereby facilitating vaginal colonization and subsequent retrograde infection of the urothelium. Our data demonstrate that females with Le(a−b−) and e(a+b−) phenotypes have a significantly higher incidence of recurrent urinary tract infections than females with a Le(a−b+) phenotype, regardless of their ABO and P blood group phenotype (p=0.002).

Further details on the panel, its uses, and further embodiments, are presented in the description which follows.

Also, antigenic modulation of cell surface structures accompanies neoplastic transformation and may precede overt histological changes. Detection of such tumor-associated antigenic changes may enhance our ability to recognize, predict or monitor the course of incipient bladder cancer. With the advent of hybridoma technology and improved immunohistochemical methodology, a number of monoclonal antibodies to bladder tumor associated antigens have been produced and characterized.

The Lewis X antigen ($Le^x$) is a cell surface differentiation antigen carried on either protein or lipid moieties. Its immunodeterminant structure is the trisaccharde galactose B 1-4 (fucose 1-3) N-acetylglucosamine which is formed by the 1--3 fucosylation of a type 2 blood group backbone chain. $Le^x$ is expressed in some normal cells including the normal proximal tubular cells of the kidney, gastrointestinal epithelia and granulocytes; it is also expressed in a number of human cancers derived from tissues that do not normally express this antigen.

Immunohistochemical studies of both frozen and deparaffinized tissue sections have not demonstrated $Le^x$ as defined by the P-12 monoclonal antibody in normal adult urothelium except in occasional umbrella cells. However, almost al papillomas and transitional cell carcinomas (TCC) express this blood group related antigen (30/33 (91%) of cases), regardless of grade, stage, blood type or secretor status of the individual.

The importance of urinary cytology in the diagnosis and surveillance of urothelial tumors is well established. But while the diagnostic accuracy of exfoliative cytology is excellent in cases of in situ (CIS) and high grade carcinoma, it is less effective in detecting the well differentiated tumors.

Moreover, the current successful treatment of germ cell tumor (GCT) has been a major advance in medical oncology. With cisplatin-based chemotherapy, 70-80% of patients with advanced GCT are cured of their disease. However, certain problems in the diagnosis and management of patients with advanced GCT persist.

Occasional seminomas exhibit pleomorphism and an increased mitotic index and may be difficult to distinguish from embryonal carcinoma by light micriscopy. There are limitations in the usefulness of criteria designated to identify patients with poor prognostic features and to select appropriate therapy. A better understanding of the biological characteristics of these tumors may aid in their classification and in selection of therapy and provide additional insight into the histogenesis of GCT.

Additionally, most of the previous studies concerning blood group-related antigens and their expression in normal and neoplastic urothelium have been performed with restricted panels of antibodies, mainly those detecting ABH and/or $Le^a$ antigens. Moreover, these studies usually lack information on secretor status of normal and neoplastic tissue samples from the same individual.

SUMMARY OF THE INVENTION

The subject invention describes a method of determining the secretor status of an individual which comprises obtaining a sample of a biological fluid from the individual and determining whether the sample includes the Lewis$^a$ and Lewis$^b$ antigens, the presence of the Lewis$^a$ antigen in the sample indicating that the individual is a nonsecretor, the presence of the Lewis$^b$ antigen in the sample indicating that the individual is a secretor, and the presence of neither antigen indicating the secretor status of the individual is inconclusive.

The invention also provides a method of further determining the secretor status of an individual of having an inconclusive secretor status which comprises determining whether the biological fluid sample from the individual includes A, B or precursor type 1 chain antigens, the presence of any such antigens in the sample indicating that the individual is a secretor, the lack of any such antigens in the sample indicating that the individual is a nonsecretor.

The biological fluid is may be, but is not limited to, saliva and plasma.

The subject application also provides a method described hereinabove, wherein the presence of $Le^a$ and $Le^b$ antigens in the biological fluid is ascertained by contacting the fluid with a panel of monoclonal antibodies having specificities for $Le^a$ or $Le^b$ antigens and determining which antibodies form complexes to the antigens in the fluid.

Furthermore, in determining the status of an individual having an inconclusive secretor status, the presence of A, B or precursor type 1 chain antigens in the biological fluid may be ascertained by contacting the fluid with a panel of monoclonal antibodies and *Ulex europaeus* lectin having specificities for A, B, or precursor type 1 chain antigens and determining which antibodies or lectin form complexes to the antigens in the fluid.

In a particularly preferred embodiment, the panel comprises the monoclonal antibodies T 174 (ATCC No. HB 8242) and T 218 (ATCC No. HB 8249), and for determining the secretor status of an individual having an indeterminate status, the panel comprises the monoclonal antibodies H 29-36 (ATCC No. HB 8248), S8 (ATCC No. HB 9036), and K 21 (ATCC No. HB 8549).

The subject invention also provides a diagnostic kit for use in determining whether an individual is a secretor which comprises monoclonal antibodies H 29-36 (ATCC No. HB 8248), S8 (ATCC No. HB 9036), T 174 (ATCC No. HB 8242), T 218 (ATCC No. HB 8249), and K 21 (ATCC No. HB 8549).

The invention provides a method of determining whether a human female subject is susceptible to an oral or urogenital infection which comprises determining whether the subject is a secretor according to the hereinabove-described methods, a secretor being susceptible to such an infection.

The present application also provides a method of distinguishing urothelial carcinoma from normal tissue which comprises obtaining a sample of biological tissue from a subject, contacting the tissue with a panel of monoclonal antibodies having specificities for A, B, $Le^a$, $Le^b$, $Le^x$, $Le^y$, or precursor type 1 chain antigens, and detecting the presence of A, B, $Le^a$, $Le^b$, $Le^x$, $Le^y$, or precursor type 1 chain antigens in the tissue by determining which antibodies form complexes, the presence of $Le^x$ antigen indicative of urothelial carcinoma, the presence of A or B antigen indicative of normal tissue, the presence of $Le^y$ antigen indicative of urothelial carcinoma in a nonsecretor, the presence of $Le^b$ and precursor type 1 chain antigen indicative of normal tissue in a secretor, and the presence of $Le^a$ antibody indicative of normal tissue in a nonsecretor.

In a particularly preferred embodiment, the panel comprises the monoclonal antibodies H 29-36 (ATCC No. HB 8248), S8 (ATCC No. HB 9036), T 174 (ATCC No. HB 8242), T 218 (ATCC No. HB 8249), P 12 (ATCC No. HB 8551), F 3 (ATCC No. HB 8217), and K 21 (ATCC No. HB 8549).

Finally, the subject application provides a method of identifying human germ cell tumor as seminoma or nonseminoma which comprises obtaining a sample of human germ cell tumor from a subject, contacting the tumor with a panel of monoclonal antibodies having specificities for $Le^a$, $Le^b$, $Le^x$, $Le^y$, or precursor type 1 chain antigens, and detecting the presence of $Le^a$, $Le^b$, $Le^x$, $Le^y$, or precursor type 1 chain antigens in the tissue by determining which antibodies form complexes, the presence of any of precursor type 1 chain, $Le^a$, $Le^b$, $Le^x$, and $Le^y$ antigen, particularly precursor type 1 chain antigen, indicative of nonseminoma.

In another form of this method, the human germ cell tumor is testicular and the nonseminoma is atypical seminoma.

In a particularly preferred embodiment, the panel comprises the monoclonal antibodies T 174 (ATCC No. HB 8242), T 218 (ATCC No. HB 8249), P 12 (ATCC No. HB 8551), F 3 (ATCC No. HB 8217), and K 21 (ATCC No. HB 8549).

BRIEF DESCRIPTION OF THE FIGURES

FIGS. 5A-L show the localization of Lewis blood group-related antigens in normal urothelium, CIS, and invasive urothelial carcinoma of the urinary bladder of a secretor.

FIGS. 9A-9B show the seminoma from Patient 28 stained with hematoxylin and eosin (left) and with monoclonal antibody K-21 to precursor structure (right).

DETAILED DESCRIPTION OF THE INVENTION

Figures 1A, 1B:
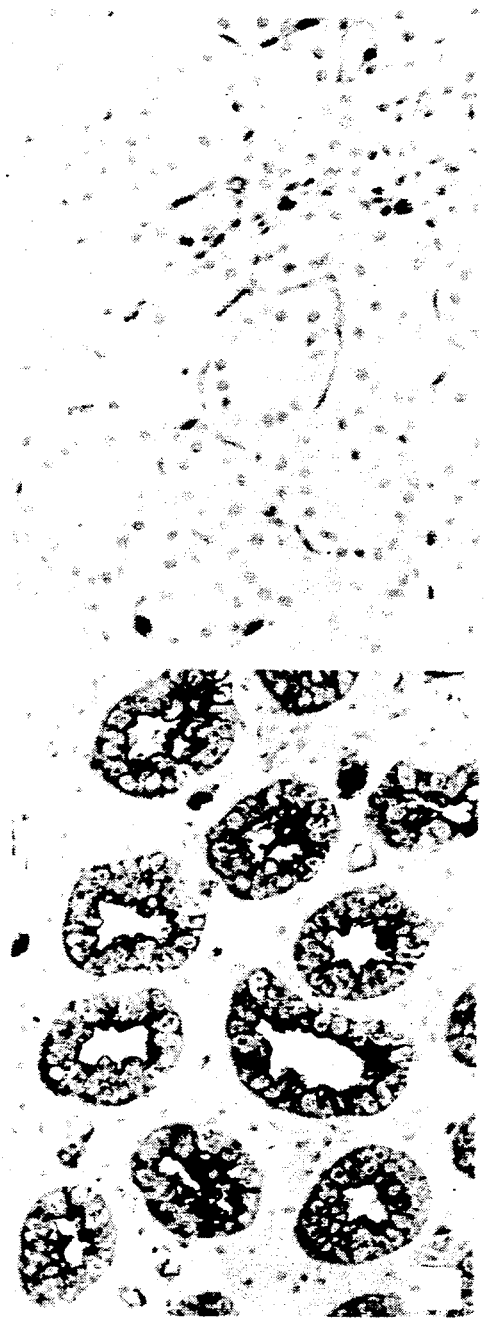
FIGS. 1A, 1B, 1C, 1D show pictorially the structures and origins of $Le^a$, $Le^b$, H-1, H-2, X, Y, A and B antigens.

The subject invention describes a method of determining the secretor status of an individual which comprises obtaining a sample of a biological fluid from the individual and determining whether the sample includes the $Lewis^a$ or $Lewis^b$ antigens, the presence of the $Lewis^a$ antigen in the sample indicating that the individual is a nonsecretor, the presence of the $Lewis^b$ antigen in the sample indicating that the individual is a secretor, and the presence of neither antigen indicating the secretor status of the individual is inconclusive.

The invention also provides a method of further determining the secretor status of an individual of having an inconclusive secretor status which comprises determining whether the biological fluid sample from the individual includes A, B or precursor type 1 chain antigens, the presence of any such antigens in the sample indicating that the individual is a secretor, the lack of any such antigens in the sample indicating that the individual is a nonsecretor.

The biological fluid is may be, but is not limited to, saliva and plasma.

The subject application also provides a method described hereinabove, wherein the presence of $Le^a$ and $Le^b$ antigens in the biological fluid is ascertained by contacting the fluid with a panel of monoclonal antibodies having specificities for $Le^a$ or $Le^b$ antigens and determining which antibodies form complexes to the antigens in the fluid.

Furthermore, in determining the status of an individual having an inconclusive secretor status, the presence of A, B or precursor type 1 chain antigens in the biological fluid may be ascertained by contacting the fluid with a panel of monoclonal antibodies and *Ulex europaeus* lectin having specificities for A, B, or precursor type 1 chain antigens and determining which antibodies or lectin form complexes to the antigens in the fluid.

In a particularly preferred embodiment, the panel comprises the monoclonal antibodies T 174 (ATCC No. HB 8242) and T 218 (ATCC No. HB 8249), and for determining the secretor status of an individual having an indeterminate status, the panel comprises the monoclonal antibodies H 29-36 (ATCC No. HB 8248), S8 (ATCC No. HB 9036), and K 21 (ATCC No. HB 8549).

In the above-described methods, the $Le^b$ antigen may be substituted by the $Le^y$ antigen.

The subject invention also provides a diagnostic kit for use in determining whether an individual is a secretor which comprises monoclonal antibodies H 29-36 (ATCC No. HB 8248), S8 (ATCC No. HB 9036), T 174 (ATCC No. HB 8242), T 218 (ATCC No. HB 8249), and K 21 (ATCC No. HB 8549).

The invention provides a method of determining whether a human female subject is susceptible to an oral or urogenital infection which comprises determining whether the subject is a secretor according to the hereinabove-described methods, a secretor being susceptible to such an infection. The infections may be but are not limited to urinary, genital, vaginal epithelial, kidney, or buccal epithelial infection.

The present application also provides a method of distinguishing urothelial carcinoma from normal tissue which comprises obtaining a sample of biological tissue from a subject, contacting the tissue with a panel of monoclonal antibodies having specificities for A, B, $Le^a$, $Le^b$, $Le^x$, $Le^y$, or precursor type 1 chain antigens, and detecting the presence of A, B, $Le^a$, $Le^b$, $Le^x$, $Le^y$, or precursor type 1 chain antigens in the tissue by determining which antibodies form complexes, the presence of $Le^x$ antigen indicative of urothelial carcinoma, the presence of A or B antigen indicative of normal tissue, the presence of $Le^y$ antigen indicative of urothelial carcinoma in a nonsecretor, the presence of $Le^b$ and precursor type 1 chain strength indicative of normal tissue in a secretor, and the presence of $Le^a$ antibody indicative of normal tissue in a nonsecretor.

In a particularly preferred embodiment, the panel comprises the monoclonal antibodies H 29-36 (ATCC No. HB 8248), S8 (ATCC No. HB 9036), T 174 (ATCC No. HB 8242), T 218 (ATCC No. HB 8249), P 12 (ATCC No. HB 8551), F 3 (ATCC No. HB 8217), and K 21 (ATCC No. HB 8549).

Finally, the subject application provides a method of identifying human germ cell tumor as seminoma or nonseminoma which comprises obtaining a sample of human germ cell tumor from a subject, contacting the tumor with a panel of monoclonal antibodies having specificities for $Le^a$, $Le^b$, $Le^x$, $Le^y$, or precursor type 1 chain antigens, and detecting the presence of $Le^a$, $Le^b$, $Le^x$, $Le^y$, or precursor type 1 chain antigens in the tissue by determining which antibodies form complexes, the presence of any of precursor type 1 chain, $Le^a$, $Le^b$, $Le^x$, and $Le^y$ antigen, particularly precursor type 1 chain antigen, indicative of nonseminoma.

In another form of this method, the human germ cell tumor is testicular and the nonseminoma is atypical seminoma.

In a particularly preferred embodiment, the panel comprises the monoclonal antibodies T 174 (ATCC No. HB 8242) T 218 (ATCC No. HB 8249), P 12 (ATCC No. HB 8551), F 3 (ATCC No. HB 8217), and K 21 (ATCC No. HB 8549).

The hybridoma cell lines which produce the monoclonal antibodies of this invention have been deposited with the American Type Culture Collection, 12301 Parklawn Drive, Rockville, Md. 20852 and bear the following accession numbers:

| Hybridoma | ATCC # |
|---|---|
| H 29-36 | HB 8248 |
| S 8 | HB 9036 |
| T 174 | HB 8242 |
| T 218 | HB 8249 |
| P 12 | HB 8551 |
| F 3 | HB 8217 |
| K 21 | HB 8549 |

Information on derivation of these hybridomas may be found in copending U.S. application Ser. No. 474,415 (H 29-36, T-174, T-218), U.S. Pat. No. 4,650,756 (S8) and U.S. Pat. No. 4,762,800 (P-12 and K-21). In addition, the hybridomas are described in Ueda, et al., *PNAS* 78:5122 (1981) (S8), Rettig, et al., *Cancer Res.* 45:815 (1985) (P-12 and K-21) and Lloyd, et al., *Immunogenetics* 17:537 (1983) (F-3). The disclosures of all of these are incorporated by reference herein.

In summary, the hybridomas are prepared following the *Kohler-Millstein* method well known to the art, using, as immunizing cell lines, the materials set forth in Table 1.

Because expression of ABO(H) antigens on the urogenital system has been discussed in the literature, e.g., Coon, et al., *Am. J. Clin. Path.* 76:163 (1981); Szulman, *J. Exp. Med.* 111:785 (1960), and studies have shown localization of $Le^a$ and $Le^b$ antigens in normal adult urothelium, Juhl, *J. Histochem. Cytochem.* 33:309 (1985), the urinary tract was used as an exemplary system. The following experiments provide an analysis which extends the study of the system to include Lewis, X, Y, and precursor determinants in the entire human urinary tract.

One skilled in the art will recognize that the analysis of human urinary tract tissue is applicable to any tissue system for the determination of expression of blood group antigens. For example, the terms "secretor" and "non-secretor" are used to define individuals who do or do not secrete A, B, or H antigens in saliva. "Secretors" produce $Le^b$ and Y antigens, whereas non-secretors produce $Le^a$ and X. Watkins, *Science* 152:172 (1966). As "secretor" or "non-secretor" status, as well as changes in this status, is considered indicative of cancer susceptibility or onset, the monoclonal antibody panels, and methods described herein, are useful in cancer diagnosis.

TABLE 1

DERIVATION AND SPECIFICITY OF MOUSE MONOCLONAL ANTIBODIES IDENTIFYING BLOOD GROUP ANTIGENS[a]

| Antibody (Ig subclass) | Immunizing cell line | Blood group specificity |
|---|---|---|
| K21 ($\mu$) | Tera-1 teratocarcinoma | Precursor (type 1 chain) |
| T174 ($\gamma$1) | SK-CO-10 colon cancer | $Le^a$ (type 1 chain) |
| T218 ($\mu$) | SK-CO-10 colon cancer | $Le^b$ (type 1 chain) |
| P12 ($\mu$) | Fresh human placenta | X (type 2 chain) |
| F3 ($\mu$) | SK-LU-3 lung cancer | Y (type 2 chain) |
| T36 ($\gamma$3) | HT-29 colon cancer | A (types 1 and 2 chains) |
| S8 ($\mu$) | SK-RC-7 renal cancer | B (type 2 chain) |

This invention is illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Material and Methods

I. SECRETORS

Tissues

Human fetal tissues ranging from 12 to 14 weeks of gestational age were obtained from elective abortions. Human normal adult tissues were obtained at autopsy within 9 hours post-mortem or from surgical pathology specimens within 1-2 hr of resection. Fresh tissues were fixed in 10% formaldehyde in phosphate buffered saline (PBS) (pH 7.4), and embedded in paraffin. Alternatively, tissues were snap-frozen in isopentane precoiled in liquid nitrogen, embedded in OCT compound in cryomolds and stored at $-70°$ C. until needed. Two fetal specimens containing kidney and ureter were studied, one expressing A group and the other H group antigens. The adult kidney, ureter, and/or bladder tissues chosen for the present study included samples from 3 group 0, 3 group A, 2 group B, and 2 group AB individuals. The blood group of individuals from whom the specimens were derived was correlated with the immunohistological patterns of reactivities.

Reagents

Purified agglutinin I from *Ulex europeus* at 4 $\mu$g/ml served to identify the H-antigen. Mouse monoclonal antibody H 29-36 recognizes A antigen (all variants), monoclonal antibody S8 detects B-antigen, monoclonal antibodies T-174, T-218, P-12 and F-3 with specificities for $Le^a$, $Le^b$, X and Y antigens, respectively, were also used. Finally, monoclonal antibody K-21 detects precursor type 1 chain antigen. The antibodies were used as undiluted culture supernatants, or after purification from mouse ascities fluid (1:250 dilution).

Immunohistochemistry a) Indirect Immunofluorescence: Frozen tissues (4 to 8 microns) were cut using a cryostat with a microtome. Cryostat-cut sections were used unfixed or fixed for 10 minutes with either 1% formalin in PBS or cold acetone. Tissue sections were washed several times in PBS and rinsed in 2% bovine serum albumin in PBS (BSA-PBS). They were then incubated in a wet chamber with primary antibodies for 1 hour at room temperature, the titration and appropriate dilution having been previously established. Sections were washed with PBS and incubated for 45 minutes with secondary fluoresceinated antibodies, which have also been previously titrated for optimal dilution (usually 1:40 in BSA-PBS). Tissue sections were washed extensively in PBS with the creation of turbulence, using a magnetic stirring plate, wet mounted in 90% glycerol in PBS, and examined with a fluorescence microscope equipped with epifluorescence, using a 100 watt mercury lamp.

b) Immunoperoxidase: Formalin-fixed and paraffin-embedded sections were deparaffinized for this technique. Sections were tested for 30 minutes in 1% hydrogen peroxide in PBS in order to remove endogenous peroxidase activity (no staining was observed when 1% periodic acid was used instead of 1% hydrogen peroxide). Tissue sections were washed several times in PBS, and then incubated with the appropriate suppressor serum for 20 minutes. Suppressor serum was drained off and sections were incubated with appropriately diluted primary antibody overnight at 4° C. Both peroxidase-antiperoxidase and avidin-biotin methods were used in these experiments. The secondary antibodies were horseradish peroxidase conjugated or biotinylated and they were incubated on sections for 1 hr. Sections were then washed several times in PBS, and rinsed with 0.05M Tris buffer, 0.1M NaCl, at pH 8. For the final reaction diaminobenzidine (DAB) was used as chromogen, and the peroxidase reaction was used as chromogen, and the peroxidase reaction was performed by incubating tissue sections for 6 to 12 minutes with 5 mg of DAB tetrahydrochloride in 100 ml of tris buffer containing 100 μg of 0.3% hydrogen peroxide. Sections were washed with distilled water, counterstained with hematoxylin, and mounted with permount.

Fresh frozen tissue sections were also used for this method. In this case, antibodies were incubated for 1 hr, and the other steps were similar to those described above for paraffin-embedded tissue sections.

c) Method for staining with lectin: The lectin *Ulex europeus* was incubated for 2 hours at room temperature, followed by rabbit and anti-Ulex lectin antibody at a dilution of 1:1000 overnight at 4° C. Immunoperoxidase methods were performed as described above using biotinylated goat anti-rabbit immunoglobulins as secondary reagent.

d) Controls: Frozen and paraffin-embedded tissues expressing the appropriate blood group antigen served for titration of the reagents as well as positive and negative controls. Negative controls included substitution of the primary antibody by another antibody of the same species and isotype, or with PBS alone.

II. HUMAN FEMALE INFECTION SUSCEPTIBILITY

Patients and Controls. The patient group consisted of 49 Caucasian women (mean age 35 years) with at least three documented urinary tract infections during a 12 month period. Five patients had a single episode of chills, fever and flank pain associated with bacteriuria. The remaining patients had symptoms of uncomplicated cystitis. All had normal intravenous urograms and cystoscopic examinations. The control group consisted of 49 Caucasian women (mean age 38.0 years) without a history of urinary tract infections.

ABO, P and Lewis Blood Group Phenotype. ABO phenotype was determined by macroscopic hemagglutination performed by incubating a drop of 4% erythrocyte suspension with two drops of anti-A, anti-B and anti-AB in three separate test tubes, respectively. Appropriate positive and negative controls accompanied each sample tested. The presence of the P1 antigen was determined by mixing one drop of the 4% erythrocyte suspension with two drops of anti-P1 serum and incubating for 15 minutes at 4° C. Macroscopic hemagglutination indicated the P1 positive phenotype. Negative and weakly positive cells were tested as controls. The Lewis blood group phenotype was determined by incubating one drop of a 4% erythrocyte suspension with two drops of anti-Le$^a$ in one test tube and a second drop of the 4% erythrocyte suspension with two drops of anti-Le$^b$ in a separate test tube at room temperature for 30 minutes. Macroscopic hemagglutination was assessed after centrifuging the test tubes at 3400 rpm for 15 seconds. The positive control for anti-Le$^a$ testing were cells with Le(a+b−) phenotype while the negative control were Le(a−b+) cells. The positive control for anti-Le$^b$ were Le(a−b+) cells while the negative control were Le(a+b−) cells.

Statistical Evaluation. Independent contingency tables were generated by considering the distributions of blood group phenotype (ABO, P and Lewis) in females with urinary tract infection and age-matched female controls. To test the hypothesis of equality of proportions between the two groups a chi-square test was used. The method of Lancaster and Irwin was applied to isolate the sources of association in contingency tables when (a) the overall chi-square test indicated non-independence between recurrent UTI and controls and (b) the blood group system had more than two phenotypes. Using their method, the overall chi-square statistics for a contingency table could be partitioned into as many components as the table had degrees of freedom. The formulae supplied by Kimball were used for obtaining the chi-square values. The critical significant value chosen was =0.05.

All the blood group phenotypes were considered together in a multivariate model, using a stepwise logistic regression, and the interactions among variables were tested.

III. URINARY BLADDER TUMORS

Tissues

Normal and neoplastic tissues were obtained from surgical pathology specimens within 1-2 hr of resection. Fresh tissues were fixed in 10% formaldehyde in PBS, pH 7.5, and embedded in paraffin.

Cystectomy specimens from 19 patients with urinary bladder tumors were obtained from the present study.

Medical histories of these patients were reviewed and Table 2 summarized patient's information, including therapy prior to cystectomy. In the majority of the cases we were able to examine normal urothelial mucosa adjacent to the tumor, urothelial mucosa distant from the tumor, carcinoma in situ and invasive urothelial carcinoma. Selection of cases were based on excellence of tissue preservation, availability of tissue blocks of normal and neoplastic urothelium, and knowledge of secretor status of the individuals under study. From two to nine tissues blocks were available on each case, and sections from every block were studied with the entire panel of antibodies. All tumors were classified by stage and histological grade and pattern. The patients included eight blood group O, six group A, three group B, and two group AB individuals. Secretor status was determined in all cases either by presence of Lewis antigens in saliva and/or in samples of peripheral blood red blood cells drawn from these patients.

Reagents

Purified agglutinin 1 from *Ulex europaeus* at 4 µg ml served to identify the H antigen. Mouse monoclonal antibody HT 29-36 (T-36) recognizing A antigen (all variants), monoclonal antibody S8 detecting B antigen, monoclonal antibodies T-174, T-218, P-12, and F-3 with specificities for $Le^a$, $Le^b$, $Le^x$, and $Le^y$ antigens, respectively, were also used. Finally, precursor type 1 chain antigen was detected by monoclonal antibody K-21. The antibodies were used as undiluted culture supernatants, or purified immunogloublin preparation at an approximate concentration of 25–40 µg/ml.

TABLE 2

Data on 19 patients with urinary bladder tumors

| Case | Age | Sex | Blood group | Lewis typing[a] | Treatment prior to cystectomy[b] | No. blocks studied |
|---|---|---|---|---|---|---|
| 1 | 62 | M | O | $Le^{a-b+}$ | TURBT | 5 |
| 2 | 76 | F | O | $Le^{a-b+}$ | TURBT | 3 |
| 3 | 59 | M | O | $Le^{a-b+}$ | M-VAC | 4 |
| 4 | 70 | M | O | $Le^{a-b+}$ | BCG/IVe Mx | 3 |
| 5 | 62 | F | A | $Le^{a-b+}$ | TURBT | 3 |
| 6 | 55 | F | A | $Le^{a-b+}$ | TURBT | 7 |
| 7 | 73 | M | A | $Le^{a-b+}$ | RTx/IVe Th | 3 |
| 8 | 53 | F | A | $Le^{a-b+}$ | TURBT | 4 |
| 9 | 40 | F | B | $Le^{a-b+}$ | TURBT | 3 |
| 10 | 73 | M | B | $Le^{a-b+}$ | TURBT/BCG | 4 |
| 11 | 60 | M | O | $Le^{a+b-}$ | RTx | 6 |
| 12 | 68 | M | O | $Le^{a+b-}$ | RTx | 5 |
| 13 | 55 | M | O | $Le^{a+b-}$ | M-VAC | 2 |
| 14 | 62 | M | O | $Le^{a+b-}$ | M-VAC | 2 |
| 15 | 55 | F | AB | $Le^{a+b-}$ | M-VAC | 2 |
| 16 | 36 | M | A | $Le^{a-b-}$ | M-VAC | 2 |
| 17 | 60 | M | A | $Le^{a-b-}$ | M-VAC | 2 |
| 18 | 59 | M | B | $Le^{a-b-}$ | RTx/M-VAC | 3 |
| 19 | 64 | M | AB | $Le^{a-b-}$ | M-VAC | 2 |

Immunohistochemistry

The method chosen for the present analysis was the avidin-biotin complex immunoperoxidase technique. Formalin-fixed and paraffin-embedded tissue sections were deparaffinized, then treated for 30 min in 1% hydrogen peroxide in PBS to remove endogenous peroxidase activity) (no staining was observed when 1% periodic acid was used instead of 1% hydrogen peroxide). Tissue sections were washed in PBS and then incubated with 10% blocking normal serum in PBS for 20 min. Blocking normal serum was drained off and sections were incubated with monoclonal antibody overnight at 4° C. The secondary antibodies were biotinylated horse anti-mouse IgG or goat anti-mouse IgM. They were incubated on sections for 1 h, the sections were then washed and incubated with the avidin-biotin complex for 30 min. The peroxidase reaction was performed by incubating tissue sections for 6–12 min with 5 mg of diaminobenzidine tetrahydrochloride in 100 ml of Tris buffer containing 100 µl of 0.3% hydrogen peroxide. Sections were washed with distilled water, counterstained with hexatoxylin, and mounted with permount.

Immunoperoxidase Analysis Using a Lectin. The lectin *Ulex europaeus* was incubated on paraffin-embedded tissue sections for 2 h at room temperature. Sections were washed with PBS and incubated with goat anti-Ulex lectin antibody (1:1000 dilution) overnight at 4° C. The immunoperoxidase method was performed as described above using biotinylated rabbit anti-goat immunoglobulins as secondary reagent.

Controls. Paraffin-embedded tissues expressing the appropriate blood group antigen were used for titration of the reagents as well as positive and negative controls. Negative controls included substitution of the monoclonal antibody by another monoclonal antibody of the same species and subtype, or incubation with PBS alone.

IV. BLADDER TUMOR

Specimens. Bladder barbotage specimens were obtained from 89 patients undergoing cystoscopy either for suspected TCC or as part of a quarterly surveillance protocol following transurethral resection of bladder tumors. The bladder was washed 7–10 times with 80–120 ml of normal saline prior to biopsy or resection. Forty control specimens were collected from 10 urologic patients undergoing cystoscopy for reasons other than bladder tumor and 30 patients with cancers of other organs who had indwelling catheters. The specimens were divided into two aliquots. One was processed for conventional cytologic examination of Papanicolaou-stained smears, while a second aliquot was fixed in an equal volume of 50% ethanol and stored at 4° C. until immunocytochemical analysis was performed.

Immunocytology. 5 ml of the ethanol fixed aliquot was centrifuged at 2500 rpm for 10 minutes and the sediment smeared on a glass slide which had been cleaned in 95% alcohol and subbed in 0.3% gelatin solution containing 0.05% chromium potassium sulfate in distilled water. The slides were fixed in cold acetone (4° C.) for ten minutes and washed in sodium phosphate buffer at pH 7.2, then treated with 0.1% hydrogen peroxide for 15 minutes at room temperature to remove endogenous peroxidase activity, rinsed several times with PBS, incubated with suppressor serum (normal goat serum, 1:10 dilution in PBS/BSA) for 15 minutes and drained. The slides were then incubated in a wet chamber with 50 lambda of P-12 anti-$Le^x$ monoclonal antibody diluted 1:8 in PBS/BSA. Control smears were incubated with an irrelevant anti-IgM antibody or PBS for 1 hour at room temperature. They were then washed 3 times with PBS and incubated in a wet chamber with biotinylated goat anti-mouse IgM (1:200 dilution in PBS) for 30 minutes, washed 3 times with PBS and incubated with a 1:100 dilution of avidin-biotin-peroxidase complex for 30 minutes in a wet chamber, washed twice in PBS and then rinsed with 0.5M Tris, 0.1M NaCl, pH 8. The peroxidase reaction was performed by incubating the cells for 5–6 minutes in 5 mg diaminobenzidine tetrachloride in 100 ml Tris buffer containing 100 ml 0.03% hydrogen peroxide. Sections were then wahed with distilled water, counterstained with hematoxylin, and mounted with Permount.

V. HUMAN GERM CELL TUMORS

Patients

Tumors from 29 patients were chosen for analysis based on (a) confirmed histological disgnosis of GCT and (b) availability of tissue blocks embedded in paraffin. Patient characteristics are summarized in Table 17.

TABLE 3

Distribution of ABO, P and Lewis Blood Group Phenotypes in 49 Females with Recurrent Urinary Tract Infections and in 49 Controls

| Phenotype | Recurrrent UTI n = 49 | Controls n = 49 | Total |
|---|---|---|---|
| $P_1$ | 39/49 (79.5%) | 37/49 (76%) | 76 |
| $P_2$ | 10/49 (20.5%) | 12/49 (24%) | 22 |
| A | 21/49 (43%) | 16/49 (33%) | 37 |
| B | 5/49 (10%) | 9/49 (18%) | 14 |
| AB | 2/49 (4%) | 3/49 (6%) | 5 |
| O | 21/49 (43%) | 21/49 (43%) | 42 |
| Le(a−b+) | 22/49 (45%) | 36/49 (74%) | 58 |
| Le(a+b−) | 14/49 (28.5%) | 9/49 (18%) | 23 |
| Le(a−b−) | 13/49 (26.5%) | 4/49 (8%) | 17 |

Patients 15 and 17-21 has Stage 1 seminoma, and the remainder of patients had advanced GCT. Two patients (patients 22 and 27) with pure seminoma at biopsy had an elevated serum α-fetoprotein level.

Tissues

The study group included cases of easily identifiable classic pure seminoma (9 cases), embryonal carcinoma (8 cases), or yolk sac tumor (2 cases). Six tumors were classified as seminomas but contained histologically atypical features (see "Results" and "Discussion"). Three additional cases exhibited mixed histologies. One patient had a mediastinal tumor interpreted as anaplastic carcinoma. Tissues from al patients were obtained with 1–2 h of resection, fixed in buffered 10% formaldehyde, dehydrated in graded alcohols and xylol, and embedded in paraffin. The tumor tissue analyzed was obtained by biopsy prior to chemotherapy or radiotherapy for all patients except Patient 11. The tumor from this patient was obtained by incomplete resection of a mediastinal mass following partial response to chemotherapy. The histology of all cases as well as their immunoreactivity were reviewed and interpreted by a reference pathologist.

Reagents

Purified agglutinin 1 from *U. europaeus* (Vector, Burlingame, Calf.) served to identify the H antigen. Mouse antibodies were used to detect the other blood group antigens as summarized in Table 5 (17, 18–22). The antibodies were used either as undiluted culture supernatants or after purification from mouse ascites fluid at approximately 20 μg/ml.

TABLE 4

Incidence of Females with Recurrent Urinary Tract Infections According to Lewis Blood Group Phenotype

| Phenotype | Number | Incidence of Females with Recurrent UTI |
|---|---|---|
| Le(a−b+) | 58 | 22/58 (38%) |
| Le(a+b−) | 23 | 14/23 (61%) |
| Le(a−b−) | 17 | 13/17 (77%) |

Immunoperoxidase. Formalin-fixed, paraffin-embedded sections were deparaffinized and treated for 15 min in 1% hydrogen peroxide in phosphate-buffered saline in order to remove endogenous peroxidase activity. Tissue sections were washed in phosphate-buffered saline and incubated with the appropriate blocking serum for 20 min, drained, and incubated with appropriately diluted primary antibody overnight at 4° C. The avidin-biotin method was used as described by Hsu et al.. The secondary antibodies were biotinylated (Vector) and incubated on section for 30 min. For the final reaction diaminobenzidine was used as chromogen, incubating tissue sections for 5 min with 5 mg of diaminobenzidine tetrahydrochloride (Sigma, St. Louis, Mo.) in 100 ml of water containing 100 μl of 0.3% hydrogen peroxide. Sections were finally washed with distilled water, counterstained with hematoxylin, and mounted with Permount.

Method for Staining with Lectin. Formalin-fixed paraffin-embedded sections were prepared as above. The *U. europaeus* lectin was incubated for 2 h at room temperature followed by rabit anti-Ulex lectin antibody (Vector) at a dilution of 1:1000 overnight at 4° C. Immunoperoxidase methods were performed as described above using biotinylated goat anti-rabbit immunoglobulins as secondary reagents.

Controls. Negative controls included replacement of the primary antibody with normal blocking serum.

RESULTS

I. Secretors

Table 1 summarizes the derivation of the panel of mouse mAb, their immunoglobulin subtype, and the characteristics of the blood group antigens detected. Table 7 summarizes the immunoreactivities of these antibodies on sections of normal adult kidney, ureter and urinary bladder. Table 6 summarizes the immunoreactivities of this panel of antibodies on sections of fetal kidney and ureter. FIGS. 1 and 2 illustrate the immunohistological staining patterns of these monoclonal antibody with normal human adult kidney and urothelium.

Blood Group Reactivities in Adult Tissues

Purified agglutinin I from *Ulex europeus* was used to identify the H-antigen. Expression of H-antigen was observed in endothelial cells and erythrocytes of all specimens studies. In the kidneys from A, B, or H individuals, H-antigen was found in the capillary network of glomeruli and also in the epithelial cells of collecting tubules with a homogeneous pattern of staining; the staining was weaker in the samples from AB individuals. All urothelial specimens expressed H-antigen throughout the mucosa, with an intense immuno-staining of the basal layers. The rest of the nephron and connective tissue were negative for Ulex reactivity in all individuals tested.

Anti-A (H 29-36) and anti-B (S8) antibodies reacted only with the appropriately matched tissue specimens, that is from blood group A positive and B positive individuals, respectively. In each case, endothelial cells and erythrocyte were found to stain with the corresponding antibody. In the kidney, A and/or B antigens were found in glomerular and peritubular capillaries and epithelial cells of collecting tubules (FIG. 1A). Urothelium was immunoreactive throughout, with some variation in staining intensity and usually greater reactivity in luminal cells (FIG. 1B).

TABLE 5

Blood group-related antigens
Purified agglutinin 1 from *Ulex europaeus* (Vector) served to identify the H antigen.

| Antibody (immunoglobulin subclass) | Immunizing cell line | Blood group specificity | CRL[a] designation | Reference |
|---|---|---|---|---|
| K21 (IgM) | TERA-1 | Precursor I | BG1 | 22 |
| T36 (IgG3) | HT-29 | A | BG2 | 19 |
| S8 (IgM) | SK-RC-7 | B | BG3 | 20 |
| T174 (IgG1) | SK-CO-10 | Lewis[a] | BG5 | 19 |
| T218 (IgM) | SK-CO-10 | Lewis[b] | BG6 | 19 |
| P12 (IgM) | Human placenta | Lewis[a] | BG7 | 22 |
| F3 (IgM) | SK-LU-3 | Lewis[b] | BG8 | 21 |

TABLE 6

| | | | Collecting ducta[a] | | | | | | | | | | | | | |
|---|---|---|---|---|---|---|---|---|---|---|---|---|---|---|---|---|
| | Blood | Secretor | PS | | | H | | | A/B | | | Le[a] | | | Le[b] | | |
| Case | Group | status | C | J | M | C | J | M | C | J | M | C | J | M | C | J | M |
| 1 | A | S | O | O' | O' | O | ◐ | ● | O' | ◐ | ● | O' | ◐ | ● | O' | ◐ | ● |
| 2 | A | | O | O | O' | O' | ◐ | ● | O' | ◐ | ● | O | ◐ | ● | O' | O' | O' |
| 3 | A | | O | O | O | O | O' | ● | O | O | ◐ | O' | ◐ | ● | O | O | O |
| 4 | A | S | O | O' | O' | O | O' | ● | O | O | ◐ | O | ◐ | ● | O | ◐ | ◐ |
| 5 | B | S | O | ◐ | ◐ | O | ◐ | ● | ◐ | ◐ | ● | O | O | O' | O | ◐ | ● |
| 6 | B | S | O | O' | O' | O | ◐ | ● | O | ◐ | ● | O | O | O | O | O | ◐ |
| 7 | B | S | O | O' | O' | O | O' | ● | O | O | ● | O | O | O | O | O' | ● |
| 8 | B | | O | O' | O' | O | O' | O' | O | O | O | O | O | O | O | O' | ◐ |
| 9 | AB | S | O | O' | O' | O | O' | O' | O | ◐ | ● | O | O | O | O | O' | O' |
| 10 | O | S | O | O | O' | O | O' | ● | O | O | O | O | O | O | O | O' | O' |
| 11 | O | S | O | O' | ● | O' | ◐ | ● | O | O | O | O | O | O | O | ◐ | ● |
| 12 | O | S | O | O' | O' | O | O' | ● | O | O | O | O | O | O | O | O | ● |
| 13 | O | | O | O | O' | O' | ◐ | ● | O | O | O | O | ◐ | O' | O | O | ◐ |
| 14 | O | S | O | O | O' | O | O | O' | O | O | O | O | O' | O' | O | O | O' |
| 15 | O | | O | O | O' | O | O' | O' | O | O | O | O | O' | O' | O | O' | O' |
| 16 | O | | O | O | O' | O | O' | O' | O | O | O | O | O' | O' | O | O' | O' |
| 17 | O | S | O | O | O' | O | O' | O' | O | O | O | O | O | O | O | O' | O' |
| 18 | O | | O | O' | ◐ | O | O' | O' | O | O | O | O | O | O | O | O | O' |
| 19 | A | NS | O | O | O' | O | O' | ◐ | O' | ◐ | ● | O | O | O | O | O' | ◐ |
| 20 | A | NS | O | O' | O | O | O | O | O | O | O | O | O | O | O | O | O |
| 21 | A | NS | O | O | O' | O | O | O | O | O | O | O | O' | O | O | O | O |
| 22 | B | NS | O | O | O' | O | O | O | O | O | O | O | O | O | O | O | O |

| | | Collecting ducta[a] | | | | | | Urothelium | | | | | |
|---|---|---|---|---|---|---|---|---|---|---|---|---|---|
| | | X | | | Y | | | | | | | | |
| Case | C | J | M | C | J | M | PS | H | A/B | Le[a] | Le[b] | X | Y |
| 1 | O | O | O | O' | ◐ | ● | O | ● | ● | ● | ● | O' | ● |
| 2 | O | O | O | ◐ | ◐ | ● | O | ● | ● | ● | ● | O' | ● |
| 3 | O | O | O | O | O' | ◐ | O | ● | ● | O' | ● | ◐ | ● |
| 4 | O | O | O | O | O' | O' | | | | | | | |
| 5 | O | O | O | ● | O | ● | O | ● | ● | O' | ● | ◐ | ● |
| 6 | O | O | O | O | O | ◐ | O | ◐ | ● | O' | ◐ | O' | ● |
| 7 | O | O | O | O | O | O' | O | ● | ◐ | O' | ◐ | O' | ● |
| 8 | O | O | O | O | ◐ | ◐ | O | ● | ● | ● | ● | ● | ● |
| 9 | O | O | O | O | O' | O' | O | ◐ | ● | O' | ● | O' | ● |
| 10 | O | O | O | O | O' | O' | O | ● | O | O' | ● | O' | ● |
| 11 | O | O | ◐ | O | O' | ● | O | ● | O | O' | ● | ◐ | ● |
| 12 | O | O | O | O | O' | ● | O | ● | O | ● | ● | O' | ● |
| 13 | O | O | O | O | O' | ◐ | O | ● | O | ● | ● | O' | ● |
| 14 | O | O | O | O | O' | O' | O | ◐ | O | O' | ● | O' | ● |
| 15 | O | O | O | O | O' | O' | O | ◐ | O | O' | ● | O' | ● |
| 16 | O | O | O | O | O | O | O | ◐ | O | ◐ | ● | ◐ | ◐ |
| 17 | O | O | O | O | O | O | O | O | O | ◐ | ● | O' | ◐ |
| 18 | O | O | O | O | O | O' | O | O | O | ◐ | ● | O' | ◐ |
| 19 | O | O | O | O | O | O' | O | ◐ | ● | O | ◐ | O | ◐ |
| 20 | O | O | O | O | O | O | O | O | ◐ | O | O | O | O |
| 21 | O | O | O | O | O | O | O | O | ◐ | ● | O | O | O |
| 22 | | | | | | | O | O | ◐ | ● | O | O | O |

TABLE 7

| | Antigen expression[a] | | | | | | | |
|---|---|---|---|---|---|---|---|---|
| Tissues | PS | H | A | B | Le[a] | Le[b] | X | Y |
| Glomerulus | OOO | OOO | OOO | OOO | OOO | OOO | OOO | OOO |
| Proximal tubule | OOO | OOO | OOO | OOO | OOO | OOO | ●●● | OOO |
| Loop of Henle | OOO | OOO | OOO | OOO | OOO | OOO | ●●● | OOO |
| Distal tubule | OOO | OOO | OOO | OOO | OOO | OOO | OOO | OOO |

TABLE 7-continued

| Tissues | Antigen expression[a] | | | | | | | |
|---|---|---|---|---|---|---|---|---|
| | PS | H | A | B | Le[a] | Le[b] | X | Y |
| Collecting duct | ●●○ | ○○○ | ●●○ | ○○○ | ○●● | ○○● | ○○○ | ○○● |
| Urothelium | ●○● | ○○○ | ●●○ | ○○○ | ●●● | ○●● | ●●● | ●●● |

Figure 2A:
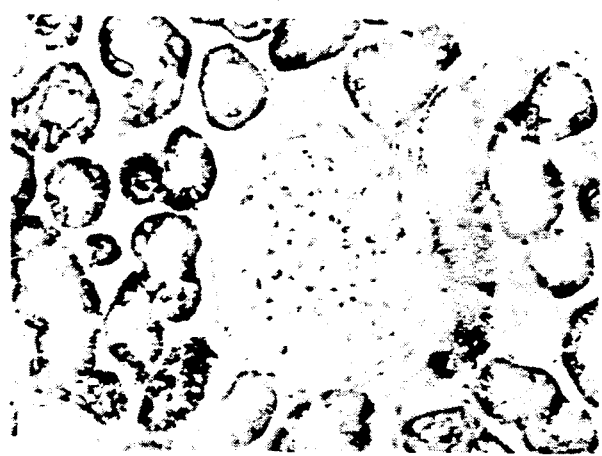
FIGS. 2A-F shows illustrate immunohistological staining patterns of monoclonal antibodies described herein, when applied to normal human adult kidney and urothelium.
Figure 2B:
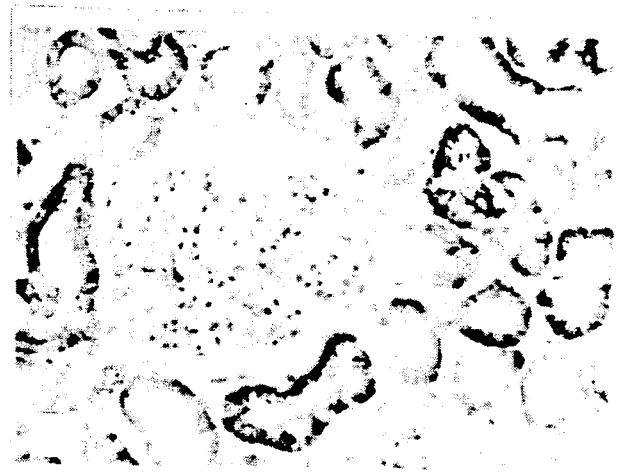
Figure 2C:
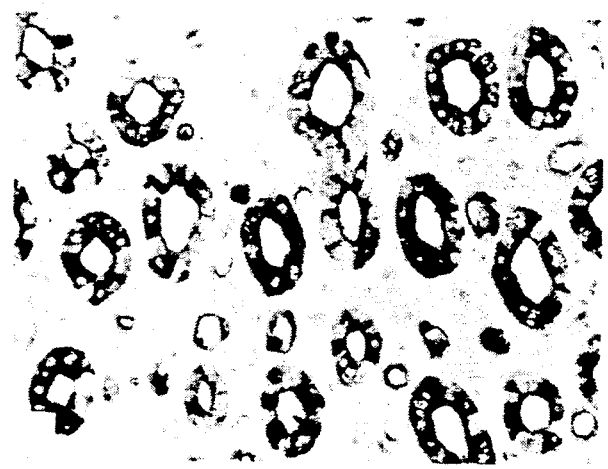
Figure 2D:
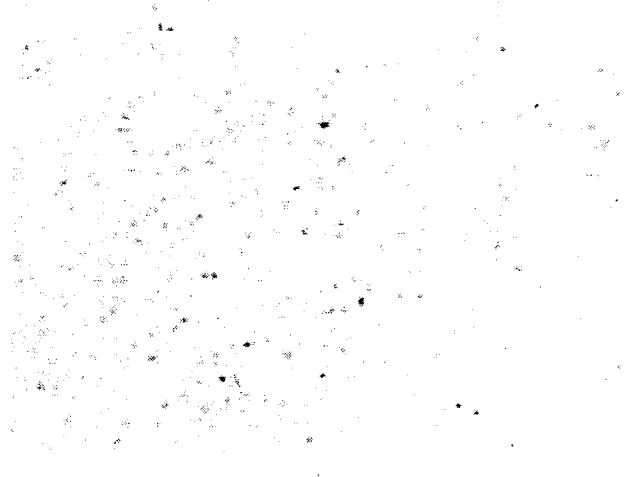
Figure 2E:
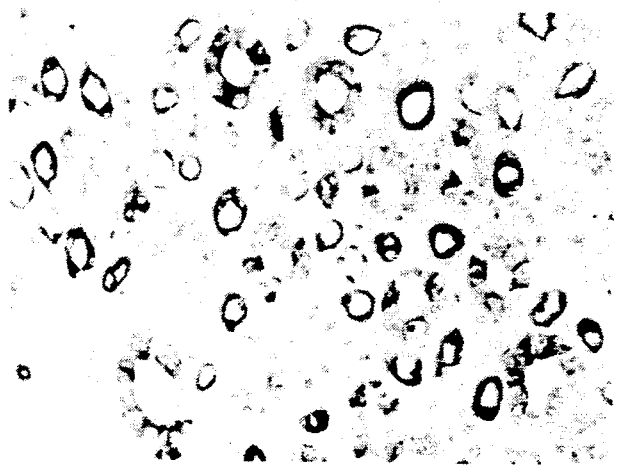
Figure 2F:
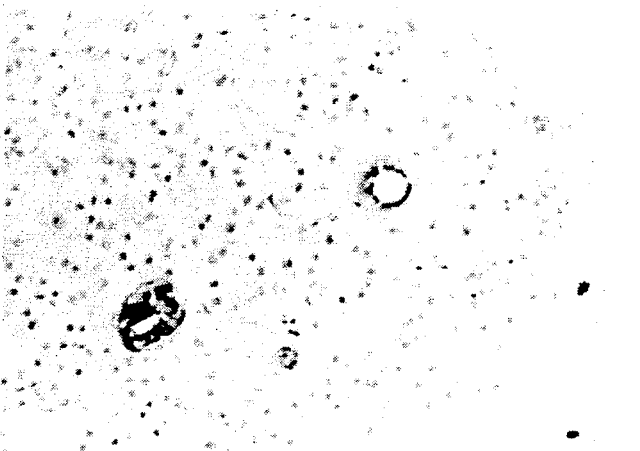

Lewis antigens were expressed on the nephron with distinct patterns of reactivities in the adult kidney. Lewis[a] (T174) was generally observed in the adult kidney in the epithelial cells of collecting and distal tubules (FIG. 2A), and in one case (AB specimen) a faint staining of the proximal tubules and portions of the Henle's loop was observed. In urothelium, Lewis[a] was found to be consistently positive in the superficial epithelial cell layers (FIG. 2B) and weak or absent in deeper cell layers, though in one sample (H specimen) there was positive staining through all layers of the epithelium. Lewis[b] (T218) was found in rare collecting ducts and sometimes single cells of the collecting duct of adult kidneys, but with intense reactivity (FIG. 2C). In urothelium, Lewis[b] was expressed mainly in the basal and suprabasal cell layers (FIG. 2D), or in some specimens throughout the entire epithelium with incrased intensity in the basal cells. X determinant (P12) was detected in polymorphonuclear leukocytes. In adult kidney, X antigen was positive in epithelial cells of proximal tubules, portions of the loop of Henle (FIG. 2E), and in one case (A specimen) faint staining of distal collecting tubular epithelial cells was observed. The reactivity of anti-X in urothelium was consistently intense in the umbrella cells, with only weak and variable staining of intermediate cell layers (FIG. 2F). Y determinant (F3) was detected in endothelial cells of capillaries in the glomeruli were immunoreactive, as were the epithelial cells of collecting ducts (FIG. 2G). The reactivity with adult urothelium was intense and Y antigen was seen as an homogenous pattern in the entire mucosa, with increased staining of basal and suprabasal cells (FIG. 2H).

Figures 1C, 1D:

Finally, the precursor type 1 chain (K21) was found in the adult kidney on occasional epithelial cells of the distal tubules and collecting ducts (FIG. 1C), and it was not detected in any specimen of adult ureter or urinary bladder studied (FIG. 1D).

BLOOD GROUP REACTIVITIES IN FETAL TISSUE

No differences were observed in the immunostaining patterns of fetal tissues when compared with those of the adult with the reagents detecting H, A, and B antigens.

In general, the expression of Le[a], Le[b], X, Y and precursor antigens in the fetal urinary tract resembled that of the adult although there were some significant differences (Table 6). Lewis[a] staining was very strong in the collecting ducts of the fetal kidney, while staining of urothelium was weaker in fetus than in adult. X antigen reactivity in the kidney was similar to the adult; the fetal urothelium was more strongly reactive than adult. Le[b] and Y antigen reactivities were very similar in adult and fetal tissues throughout the urinary system.

Finally, in contrast to adult tissues, fetal kidney and ureter expressed precursor type 1 antigen as strong and homogenous staining of epithelial cells of collecting tubules and urothelium.

One skilled in the art will see the applicability of the monoclonal antibodies and panels of monoclonal antibodies described herein. For example, tissues and organs may be typed according to expression of blood group antigens to determine if they may be used in tranplantation. The blood group antigen profile of the organ and/or tissue to be transplanted is compared to the blood group antigen profile of the intended recipient to determine if cross reactivity is to be expected. Blood typing can be done also, again using the antibodies and antibody panels described herein. A sample of blood is contacted to an antibody or panel of antibodies under conditions which favor complexing of the blood group antigens present with the known antibodies. By examining the pattern of complexing, one therefore determines the presence, or lack thereof, of particular blood group antigens. In typing organs and tissues, a similar practice is used (i.e., a cell sample or tissue sample is used for the contacting to the antibodies.

One skilled in the art will also see that in cancer patients, blood group antigen expression often changes, and different changes are characteristic of particular cancerous conditions. Thus, when cancer is suspected, a patient's blood, body secretions, or samples of tissue, are assayed using the monoclonal antibodies and antibody panels of this invention. Following the contacting method described supra, a pattern of blood group antigen expression is obtained, which is compared to an individual's normal blood group antigen expression panel, or "blood type". A diagnosis can then be made regarding the patient's condition with respect to cancer.

Hence, by using a panel of monoclonal antibodies including at least one antibody from the group consisting of H 29-36, S-8, T-174, T-218, P-12, F-3, and K-21, the aforementioned aspects of this invention are accomplished. As will be seen, supra, this invention is particularly useful in diagnosing cancer of the larynx, respiratory tract, and urinary bladder or urinary tract cancer.

One skilled in the art will see also that the antibodies and panel of antibodies described herein can be obtained in the form of kits, wherein different samples of monoclonal antibodies are separately packaged, such that individual antibodies, or the entire panel may be used, as desired. The individual samples allow one to perform sequential testing, for example.

II. HUMAN FEMALE URINARY TRACT INFECTIONS

ABO Blood Group Phenotype. Of the 49 patients with recurrent urinary tract infections, 21 (43%) were blood type A, 5(10%) blood type B, 2 (4%) blood type AB and 21 (43%) blood type O. The distribution in the 49 controls was 16 (33%) blood type A, 9 (18%) blood type B, 3 (6%) blood type AB and 21 (43%) blood type O (Table 3). The difference in the proportions of A, B, AB and O phenotypes in the control and infection groups was not statistically significant ($X^2=2.019$, $df=3$, $P=0.598$).

P Blood Group Phenotype. Of the 49 patients with recurrent urinary tract infections, 39 (79.5%) were $P_1$ blood type and 10 (20.5%) were $P_2$ blood type. In the control group 37/49 (76%) were $P_1$ and 12/49 (24%) were $P_2$ blood type respectively (Table 3). The proportions of $P_1$ and $P_2$ did not differ significantly in the control and infection group ($X^2=0.234$, df=1, $P=0.628$). Overall, of the 76 patients with $P_1$ blood type, 39 (51%) had recurrent urinary tract infections while 37 (49%) were controls. Of the 22 $P_2$ females, 10 (45.5%) had recurrent infections while 12 (54.5%) were controls.

Lewis Blood Group Phenotype. The distribution of Lewis blood group phenotypes among the 49 patients with recurrent urinary tract infections was 22 (45%) Le(a−b+), 14 (28.5%) Le(a+b−) and 13 (26.5%) Le(a−b−). The distribution of Le(a−b+), Le(a+b−) and Le(a−b−) in the 49 women comprising the control group was 36 (74%), 9(18%) and 4(8%), respectively (Table 3). The difference in the proportions of Le(a−b+), Le(a+b−) and Le(a−b−) phenotypes in the control and infection groups was statistically significant ($X^2=9.231$, df=2, $P=0.002$).

The proportions of Le(a+b−) and Le(a−b−) in the control and infection groups are not statistically different ($X^2=0.952$, df=1, $P=0.329$). Therefore, we can combine these two phenotypes and compare this combined group to Le(a−b+) individuals. The proportions of the combined Le(a+b−)/Le(a−b−) phenotypes and Le(a−b+) phenotype in the control and infection groups are statistically different ($X^2=8.279$, df=1, $P=0.002$).

Only 22 of 58 (38%) females with Le(a−b+) phenotype had recurrent urinary tract infections, while 14 of 23 (61%) females with Le(a+b−) phenotype and 13 of 17 (77%) with Le(a−b−) phenotype had recurrent infections (Table 4).

The results of the multivariate analysis confirmed the findings of the univariate analysis: only Lewis blood group phenotypes were selected into the equation. Furthermore, no interaction among variables significantly increased the prediction of a patient's susceptibility to recurrent urinary tract infections.

DISCUSSION

Predisposition to urinary tract infections and other infectious diseases has been associated with ABO blood group and secretor status. While ABH blood typing identifies the ABO phenotype, Lewis blood typing can identify the secretor status of most individuals in addition to the Lewis antigen phenotype. Expression of either Le(a+b−) or Le(a−b+) requires the presence of at least one dominant allele of the dimorphic Lewis gene (LeLe or Lele). Individuals who are Le(a−b+) are secretors (SeSe or Sese) and account for approximately 76% of the population, while Le(a+b−) are nonsecretors (sese) and account for approximately 18% of the population. The remaining 6% of the population are homozygous recessive for the Lewis gene (lele) and are phenotypically Le(a−b−). These individuals may be either secretors or nonsecretors and would require examination of blood substances in saliva to categorize.

Figure 3:
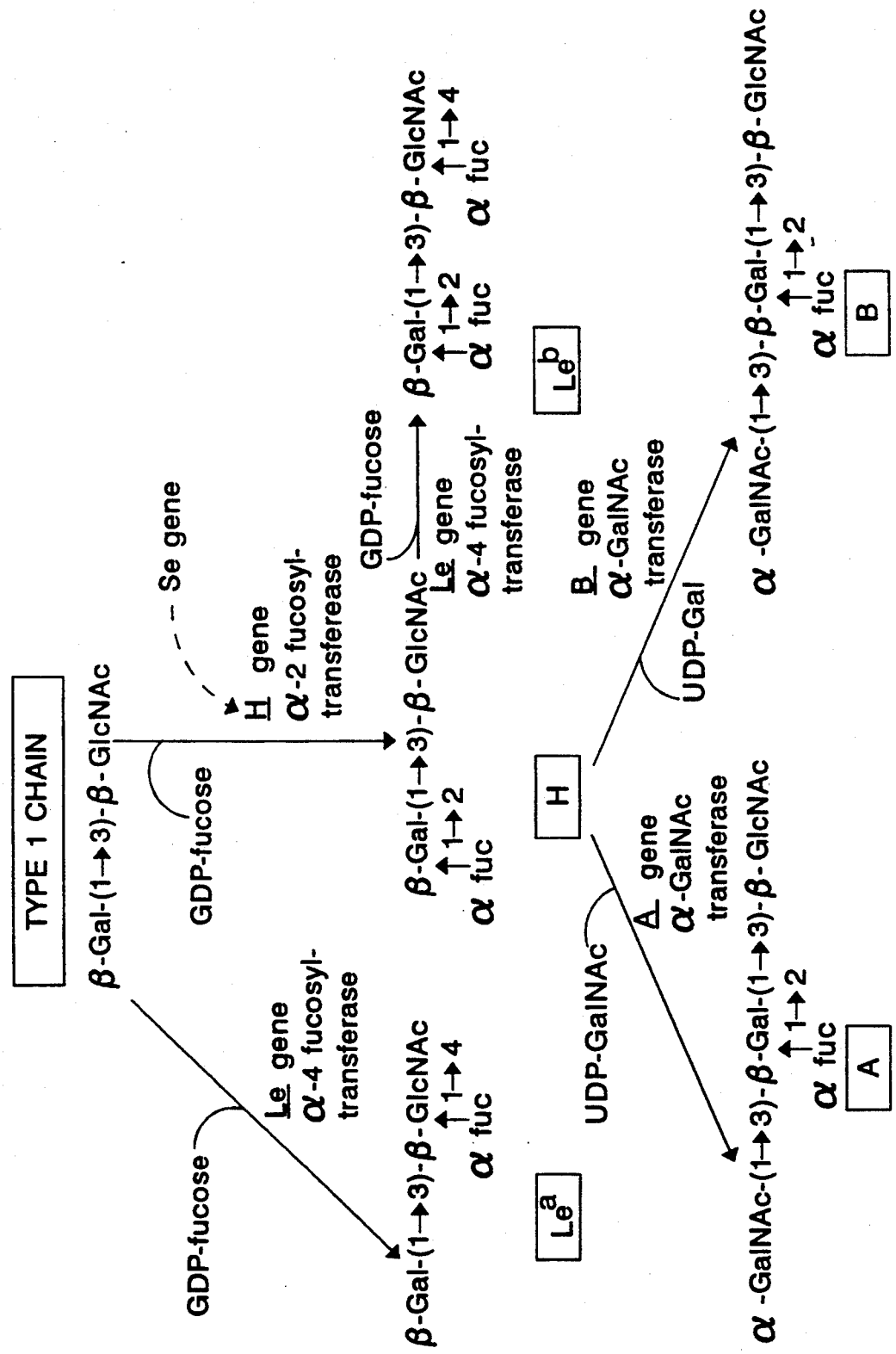
FIG. 3 illustrates the genetic and biosynthetic pathways of type 1 blood group antigens in humans.

The 4-fucosyltransferase synthesized by the Le gene converts precursor type 1 chain to $Le^a$ by addition of a fucose residue (FIG. 3). However, in the presence of the H gene and its regulatory Se gene, precursor type 1 chain is preferentially converted to H substance by the addition of a fucose via the H controlled 2-fucosyltransferase. H substance, itself a potential precursor structure, can then be converted to $Le^b$, a difucosylated structure, by the addition of a second fucose by the 4-fucosyltransferase controlled by the Le gene; or to A and B determinants in the presence of the appropriate gene and its specific glycosyltransferase (FIG. 3).

The immunoanatomic distribution of type 1 blood group antigens in human urothelium is influenced by the individual's ABO, Lewis and secretor phenotype. The urothelium of most secretor individuals and occasional nonsecretors express the $Le^a$ determinant if they possess at least one dominant Le allele. While the urothelium of secretor individuals is very rich in A, B, H and $Le^b$ determinants, these antigens are not detected in the urothelium of nonsecretors due to their inability to fucosylate precursor type 1 chain to H substance. $Le^y$ determinant, a difucosylated type 2 blood group antigen, is not detected in the urothelium of nonsecretors, but is present in that of secretors. The urothelium of most Le(a−b−) individuals has minimal or no $Le^a$ or $Le^b$ reactivity.

Our study indicates that nonsecretor females, i.e., Le(a+b−) and those who are Le(a−b−) have a significantly higher incidence of recurrent urinary tract infections then Le(a−b+) females (p=0.002), regardless of red cell ABO and P phenotype. This suggests a decreased availability of putative receptors for $E.$ $coli$ in Le(a−b+) individuals. The protective effect is most likely due to fucosylated structures at the cell surface and to the permissive effect of the secretor gene, allowing the blood group biosynthetic pathway to proceed beyond the precursor structures. Two independent studies support this hypothesis. Lomberg showed increased binding ability of bacterial adhesins to epithelial cells from nonsecretors compared to secretors and suggested a shielding of receptors by the products of the secretor gene. Schaeffer found that incubating pathogenic $E.$ $coli$ with mannose or some of its derivatives inhibited their adherence to uroepithelial cells, whereas incubation with L-fucose did not. This demonstrates that while pathogenic $E.$ $coli$ bind to mannose and their derivatives, they do not bind to fucose, a very closely related six carbon saccharide. The presence of exposed fucosylated determinants such as H, $Le^a$, $Le^b$ and $Le^y$ on the urothelium of secretor individuals thus appears to protect it from bacterial adherence, while nonsecretors, who do not have detectable levels of H, $Le^b$ or $Le^y$ on their urothelial cell surface, are at increased risk. The protective effect of secretor status is particularly conspicuous in B individuals. Only 2 of 10 B secretors had recurrent urinary tract infections. This suggests that in addition to fucosylated structures found in all secretors, galactose, the saccharide added by the D-galactosyltransferase encoded by the B gene may also be important in preventing bacterial adherance. This is consistent with Schaeffer's observation that $E.$ $coli$ does not bind to galactose. Nonsecretor B individuals, who are unable to synthesize the fucosylated intermediate H substance, therefore do not express B antigen on their urothelium.

The role of P blood group phenotype in recurrent urinary tract infections is controversial. Mullholand found a predominance of $P_2$ females with recurrent cystitis. However, Lomberg found that $P_1$ individuals had a higher incidence of urinary tract infections and recurrent pyelonephritis due to attaching bacteria in reflux-free patients. The Gal 1-4GalB disaccharide, a component of the P blood group antigen, is known to bind certain uropathogenic bacteria. Lomberg speculated that this disaccharide was increased in $P_1$ individuals and responsible for increased bacterial adherence. However, recent evidence suggests that the amount of Gal 1-4GalB containing glycolipids in uroepithelial cells is not different between $P_1$ and $P_2$ individuals. Our data do not show a significant difference in the rate of recurrent urinary tract infections in $P_1$ or $P_2$ individuals when compared to $P_1$ and $P_2$ controls.

The results of the present study demonstrate that females with Le(a−b−) and Le(a+b−) phenotypes have a significantly increased incidence of recurrent urinary tract infections. Lewis blood typing may identify patients at increased risk for urinary track infections and provide a useful parameter by which to base prophylactic antibiotic therapy.

III. URINARY BLADDER TUMORS

Table 1 summarizes the derivation of the panel of monoclonal antibodies, their immunoglobulin subtype, and their specificity for blood group antigens. Tables 11 and 13 summarize the clinical information and immunoreactivities of these antibodies on sections of normal urothelium, carcinoma in situ, and invasive urothelial carcinoma of the urinary bladder, correlating blood type and secretor status of the individuals. FIGS. 4–6 illustrate the immunohistological staining patterns of these monoclonal antibodies with normal urothelium, carcinoma in situ of the urinary bladder, and invasive urothelial carcinomas.

Blood Group Expression in Normal Adult Urothelium

As previously reported, antibodies detecting blood group antigens were found to be differentially expressed in normal urothelium of secretor and nonsecretor individuals. Tables 11 and 13 include the reactivities observed in tissue sections of histologically normal human urothelium from all individuals analyzed in the present study: $Le^{a-b+}$ (secretors), $Le^{a+b-}$ (nonsecretors), and $Le^{a-b-}$ (secretors or nonsecretors) individuals.

Anti-A (T36) and anti-B (S8) antibodies reacted only with tissue specimens from blood group A-positive and B-positive individuals respectively. They were also expressed by the two AB individuals tested. In each case, endothelial cells and erythrocytes were found to stain with the corresponding antibody or antibodies. Urothelium of secretors was immunoreactive throughout (FIG. 4A) with some variation in staining intensity and usually greater reactivity in basal cells. Urothelium of the one evaluable nonsecretor (Case 15) was group AB and unreactive for both A and B antigens. Urothelium of $Le^{a-b-}$ individuals (Table 13) showed strong A and weak B antigenic profiles.

Expression of H antigen was observed in endothelial cells and erythrocytes of all specimens studied, regardless of secretor status as previously described. Histologically normal urothelium of type O secretors expressed H antigen either throughout the mucosa (FIG. 4D) or with intense immunostaining of the basal layers. H antigen was undetected in normal urothelium of four type A secretors and there was patchy staining in one of two type B secretors (Table 11). In the nonsecretors, there was staining of basal epithelium in two of four type O cases (FIG. 4G) and on staining the AB case.

Lewis antigens were expressed on normal urothelium with distinct patterns of reactivities. Lewis$^a$ (T174) in secretors was found to be positive in the superficial epithelial cell layers and weak or absent in deeper cell layers in eight patients (FIG. 5A), while in two samples, both from type A patients, there was no staining of the

TABLE 11

| Case | BG[a] type | PSI[b] N | C | T | H N | C | T | A N | C | T | B N | C | T | Le[a] N | C | T | Le[b] N | C | T | Le[a] N | C | T | Le[b] N | C | T |
|---|---|---|---|---|---|---|---|---|---|---|---|---|---|---|---|---|---|---|---|---|---|---|---|---|---|
| 1 | O | | | | | | | | | | | | | | | | | | | | | | | | | |
| 2 | O | | | | | | | | | | | | | | | | | | | | | | | | | |
| 3 | O | | | | | | | | | | | | | | | | | | | | | | | | | |
| 4 | O | | | | | | | | | | | | | | | | | | | | | | | | | |
| 5 | A | | | | | | | | | | | | | | | | | | | | | | | | | |
| 6 | A | | | | | | | | | | | | | | | | | | | | | | | | | |
| 7 | A | | | | | | | | | | | | | | | | | | | | | | | | | |
| 8 | A | | | | | | | | | | | | | | | | | | | | | | | | | |
| 9 | B | | | | | | | | | | | | | | | | | | | | | | | | | |
| 10 | B | | | | | | | | | | | | | | | | | | | | | | | | | |

[a]BG, blood group.
[b]Analysis of formalin-fixed paraffin-embedded tissue sections using immunoperoxidase techniques (avidin-biotin). N, normal urinary bladder. C, carcinoma in situ. T, primary urinary bladder invasive tumor. PS, blood group precursor substance.
[c]●, homogeneously stained; ◐, basal immunostaining; ◉, luminal immunostaining; ◍, heterogeneously stained; ○, undetectable immunoreactivity.
[d]Immunoreactivity was observed only in occasional umbrella cells.

TABLE 12

| Case | BG type | PSI[a] N | C | T | H N | C | T | A N | C | T | B N | C | T | Le[a] N | C | T | Le[b] N | C | T | Le[a] N | C | T | Le[b] N | C | T |
|---|---|---|---|---|---|---|---|---|---|---|---|---|---|---|---|---|---|---|---|---|---|---|---|---|---|
| 11 | O | | | | | | | | | | | | | | | | | | | | | | | | | |
| 12 | O | | | | | | | | | | | | | | | | | | | | | | | | | |
| 13 | O | | | | | | | | | | | | | | | | | | | | | | | | | |
| 14 | O | | | | | | | | | | | | | | | | | | | | | | | | | |
| 15 | AB | | | | | | | | | | | | | | | | | | | | | | | | | |

TABLE 13

Figure 4A:
FIGS. 4A-I show the localization of blood group A and H antigens in normal urothelium, CIS, and invasive urothelial carcinoma of the urinary bladder of two secretors and a nonsecretor.
Figure 4B:
Figure 4C:
Figure 4D:
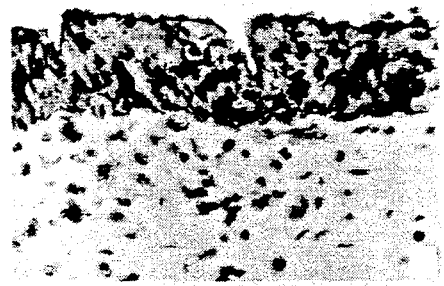
Figure 6A:
FIG. 6A-6L show the localization of Lewis blood group-related antigens in normal urothelium, CIs and invasive urothelial carcinoma of the urinary bladder of a nonsecretor.
Figure 6B:
Figure 6C:
Figure 6D:
Figure 6E:
Figure 6F:
Figure 6G:

| Case | BG type | PSI[a] N | C | T | H N | C | T | A N | C | T | B N | C | T | Le[a] N | C | T | Le[b] N | C | T | Le[a] N | C | T | Le[b] N | C | T |
|---|---|---|---|---|---|---|---|---|---|---|---|---|---|---|---|---|---|---|---|---|---|---|---|---|---|
| 16 | A | | | | | | | | | | | | | | | | | | | | | | | | | |
| 17 | A | | | | | | | | | | | | | | | | | | | | | | | | | |
| 18 | B | | | | | | | | | | | | | | | | | | | | | | | | | |
| 19 | AB | | | | | | | | | | | | | | | | | | | | | | | | | | urothelium. In nonsecretors, Lewis$^a$ showed at least patchy reactivity in three of four group O cases (FIG. 6A) and was negative in one group O and one group AB case, while in Le$^{a-b-}$ individuals staining was observed only in the one group B case. Lewis$^b$ (T218) was expressed in the urothelium of all secretors with intense immunoreactivity (FIG. 4D). Three of five nonsecretors lacked expression of Lewis$^b$ in their normal urothelium, while the remaining specimens showed patchy staining, mainly found in basal and suprabasal cell layers (FIG. 6D). Expression of Le$^b$ parallel that of Le$^a$ in Le$^{a-b-}$ individuals, being only partially immunoreactive in two cases and negative in two cases (Table 13). The reactivity of anti-Le$^x$ (P12) was absent or weak except for an occasional umbrella cell, regardless of secretor status (FIGS. 5G and 6G). Le$^y$ determinant (F3) was detected in endothelial cells and erythrocytes in O individuals. The reactivity with normal urothelium of secretors was intense and homogenous (FIG. 5J), with the exception of one case in which only patchy staining was observed (A specimen) (Table 11). Nonsecretor individuals either lacked expression of Le$^y$ determinant (four of five cases) (FIG. 6J) or showed patchy basal staining in the urothelium. Of the four Le$^{a-b-}$ individuals, two showed luminal immunoreactivities and the other two were unreactive.

Finally, the precursor type 1 chain (K21) was not detected in any normal urothelium of secretor individuals (Table 11). However, immunoreactivity was observed in one of five nonsecretors and one of four Le$^{a-b-}$ individuals, mainly in basal and supra-basal cell layers.

Blood Group Expression in Areas of Neoplastic Urothelium

Table 2 summarizes patient's age, sex, blood group type, secretor status, treatment prior to this study, and number of blocks analyzed. Tables 11 and 13 summarize immunoreactivities observed in the normal urothelium compared with in situ and invasive carcinoma from the same individual.

Blood Group Antigens in Flat in Situ and Noninvasive Papillary Carcinoma

Figure 4E:
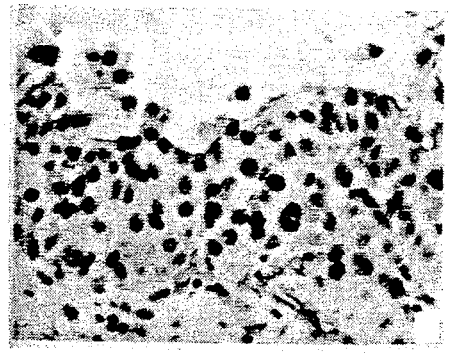
Figure 4F:
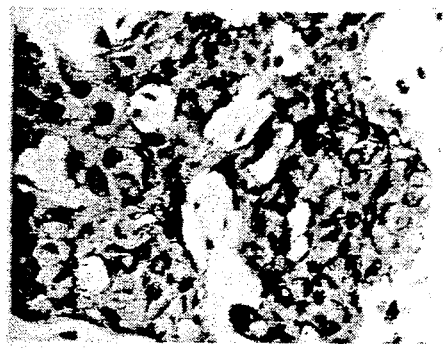
Figure 4G:
Figure 4H:
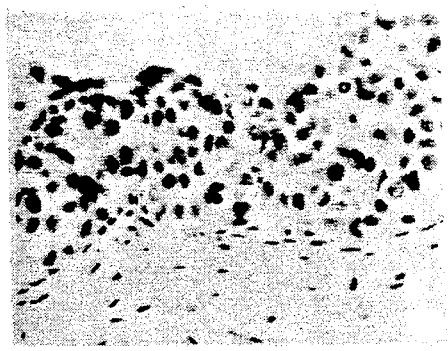
Figure 4I:
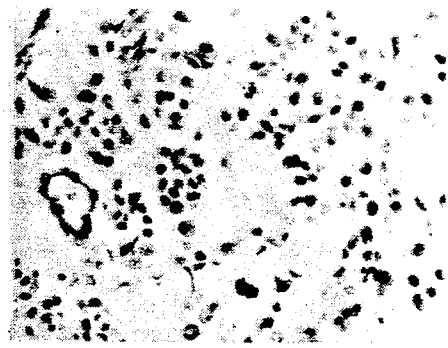

Areas of CIS were identified in 14 of 19 cases; the appropriate blood group antigen was expressed in normal epithelium of 11 of the 14 cases. Deletion of ABH antigens was noted in the neoplastic epithelium of seven of these 11 cases (FIG. 4B). The remaining four cases showed variable and patchy patterns of reactivities (FIG. 4E). In one case (type A specimen, Le$^{a-b-}$ individual) (Case 17) H antigen was expressed homogeneously throughout the in situ and invasive tumor but only in luminal epithelium in benign areas. It should be emphasized that some nonsecretor individuals lacked expression of these antigens in their normal urothelium, leaving only two evaluable cases with areas of CIS to study in individuals expressing the antigen in normal epithelium. Two type O nonsecretors were negative for H antigen in areas of CIS, as well as in normal mucosa (Cases 11 and 14) (FIG. 4H). An AB nonsecretor was unreactive for H, A, and B antigens in normal and all neoplastic urothelium. Specimens from Le$^{a-b-}$ individuals showed variable patterns of immunoreactivities.

Lewis$^a$ antigen in areas of CIS did not differ appreciably from normal urothelium in the majority of the cases. It was expressed in seven of nine secretors, one of three nonsecretors (FIG. 6B), and one of two Le$^{a-b-}$ individuals. The pattern of reactivity was luminal, as in the normal urothelium, or patchy. The remaining cases, two secretors (FIG. 5B), two nonsecretors, and one Le$^{a-b-}$ individual, were unreactive for the Le$^a$ determinant.

Lewis$^b$ antigen was homogeneously stained in areas of CIS in three of nine secretors (FIG. 5E), while in the remaining cases there was heterogeneous reactivity. Similarly, in nonsecretors and Le$^{a-b-}$ individuals Le$^b$ expression mimiked that of normal urothelium, being positive in two of five cases (FIG. 6E).

Figure 6H:

Lewis$^x$ determinant expression appeared in areas of CIS in seven of nine secretor individuals, showing a strong and patchy distribution (FIG. 5H). Two of three nonsecretors and the two Le$^{a-b-}$ individuals who were tested were immunoreactive with a heterogeneous pattern of staining (FIG. 6H).

Lewis$^y$ determinant was universally expressed in all areas where CIS was identified, regardless of blood type and secretor status. Uniform immunoreactivity was observed in six of 14 patients and variable staining occurred in the remaining eight (FIGS. 5K and 6K). Thus, expression was similar to that seen in normal urothelium. However, in two nonsecretors and one Le$^{a-b-}$ patient areas of CIS were positive whereas the normal tissue was negative.

Precursor type 1 chain determinant was absent in areas of CIS in 13 of 14 cases in which it could be evaluated. One O-type nonsecretor showed patchy immunoreactivity.

Blood Group Antigens in Invasive Bladder Tumors

A antigen of tumor cells was deleted in three of four A-type secretors (FIG. 4C), and diminished in the other one, which showed heterogeneous staining. It was similarly diminished on invasive tumor cells in the two A-type Le$^{a-b-}$ individuals. A antigen was undetected in the AB-type nonsecretor, and lost on invasive tumor cells in the AB-type Le$^{a-b-}$ patient.

B antigen was deleted in tumor cells of the two B-type secretor cases and a B-type Le$^{a-b-}$ individual. The AB-type nonsecretor was unreactive for B antigen, whereas the AB-type Le$^{a-b-}$ individual showed patchy expression of B antigen in a subpopulation of tumor cells.

H antigen was homogeneously expressed in invasive urothelial carcinoma in three of 19 cases (FIG. 4F), while patchy immunoreactivity was observed in 10 cases. Three O-type, one A-type, one B-type, and one type-AB cases lacked H antigen reactivity in invasive tumor (FIG. 4I), but in five of these six cases the normal urothelium was also nonreactive so this could not be considered an antigenic deletion.

Lewis$^a$ antigen was expressed by tumor cells in seven of 10 secretors and three of nine cases of nonsecretor and Le$^{a-b-}$ individuals. In five cases Le$^a$ antigen was present in normal urothelium and deleted in invasive tumor cells (FIG. 5C). In three cases it was expressed in tumor but not in normal epithelium. The immunoreactivities observed were heterogeneous in most cases, but diffuse immunostaining was found in two B and one A type specimens (FIG. 6C).

Lewis$^b$ antigen was expressed by invasive tumor cells in all secretor cases (FIG. 5F), with various patterns of reactivities. Six of 10 cases were homogeneously stained and the rest showed patchy staining. There was staining in three of nine nonsecretor and Le$^{a-b-}$ cases, the same cases that stained in areas of CIS and/or in normal urothelium (FIG. 6F).

Figure 6I:
Figure 6J:
Figure 6K:

Lewis$^x$ determinant was expressed by tumor cells in all secretors, nonsecretors and Le$^{a-b-}$ individuals, showing variable heterogeneity in their immunophenotypic patterns (FIG. 5I and 6I). Staining was homogeneously positive in four cases, and heterogeneous in the others; in the former there was an enhanced antigenic expression in the invasive tumor as compared to the corresponding CIS. In all these cases normal urothelium was Le$^x$ antigen negative or showed only staining of occasional surface umbrella cells (see above).

Figure 6L:

Lewis$^y$ determinant was detected in the invasive tumor of all cases under study as it was in CIS, regardless of blood type and secretor status. Secretor individuals usually showed diffuse immunoreactivity, that is staining in 80-100% of invasive tumor cells (FIG. 5L). Nonsecretors and Le$^{a-b-}$ individuals had either enhanced expression of Le$^y$ antigen in invasive tumor cells when compared to their normal urothelium (three of nine cases) or neosynthesis of Le$^y$ antigen in the invasive tumor when the Le$^y$ determinant was undetectable in their normal urothelium (six of nine cases) (FIG. 6L).

Precursor type 1 chain determinant showed patchy expression by invasive tumor cells in five of 10 secretors, one of five nonsecretors, and three of four Le$^{a-b-}$ individuals. In nonsecretors and Le$^{a-b-}$ individuals, two of the positive cases for antiprecursor antibody showed no reactivity for anti-H antibodies, while three of five negative cases for precursor type 1 determinant stained for H antigen.

DISCUSSION

In this report we describe a detailed immunohistological analysis of normal human urothelium and transitional cell carcinomas using an extensive panel of reagents detecting precursor A, B, H, Le$^a$, Le$^b$, Le$^x$, and Le$^y$ blood group antigens. The reactions with each reagent were compared in consecutive tissue sections of normal and tumor samples of individuals with known blood type and secretor status (saliva and/or Lewis typing studies). This analysis of blood group antigen phenotypes in human urothelium is an extension of our earlier studies on the human nephron.

Changes in blood group-related antigen expression in the urogenital system have been extensively discussed in the literature. Pioneering studies were based on an RCA test to detect such antigens in normal and neoplastic urothelium. With this method neoplastic urothelium was reported to show deletion of A, B, and/or H antigens, and antigen deletion was said to precede or be predictive of tumor invasion. With the recent technical improvements in immunohistochemistry and the availability of antibodies detecting ABH antigens, these early observations were reexamined. Immunohistological methods proved to be more sensitive than the red cell adherence test, and minimized the false-negative results that characterized the latter.

In the present study we have observed either complete or partial deletion of ABH antigens in areas of CIS, independently of blood type and secretor status. However, since a subgroup of nonsecretors lack expression of H antigen in normal urothelium, the lack of expression in areas of CIS in these individuals should not be considered a deletion phenomenon. Incompatible blood group expression (e.g., A blood group antigen in O or B individuals) was not observed in CIS. Le$^a$ and Le$^b$ immunoreactivity in CIS paralleled that in normal urothelium; only in a few cases was Le$^a$ detected in CIS of individuals with undetectable levels in the normal urothelium. Le$^x$ and Le$^y$ determinants usually showed either increased expression or neosynthesis in CIS. In the case of Le$^y$ antigen, these phenomena were mainly observed in nonsecretor and Le$^{a-b-}$ individuals. Expression of Le$^x$ and Le$^y$ antigens was considered a neosynthesis phenomenon when the normal mucosa showed undetectable levels of these antigens. Precursor type 1 structure was expressed in only one case with CIS.

Invasive bladder tumor cells usually showed deletion of A and B antigens. However, neither al tumors nor all cells within a given tumor showed complete deletion of ABH determinants. Absence of A and/or B antigens could be due to lack of the corresponding glycosyltransferases, which in turn could result in an accumulation of both H and precursor molecules. Using the red cell adherence test, Limas and Lange reported increased reactivity for H antigen in patients of blood group A or B, whereas A or B isoantigens were reduced or absent. In the present study, 68% of invasive tumors expressed H antigen, and 47% showed heterogeneous immunoreactivities for the precursor type 1 structure. It should be noted that, in general, cases in which invasive tumor cells were strongly reactive for anti-H did not react intensely for anti-precursor antibody, and vice versa. Again, enhanced fucosylation of the precursor could explain the increased immunoreactivity of the H antigen seen in some cases, while lack of fucosylation could explan absence of H antigen and expression of precursor type 1 molecule in other cases.

Lewis$^a$ and Lewis$^b$ determinants in general are expressed in invasive tumor cells and CIS, as in the normal urothelium. However, in five cases, Le$^a$ showed downregulation, being detected on normal urothelium but not on invasive tumor cells. Expression on tumor cells of Le$^a$ and/or Le$^b$ structures in Le$^{a-b-}$ and Le$^{a+b-}$ RBC-typed individuals was not totally unexpected and has been reported in gastrointestinal and normal urothelium.

The Lewis$^x$ determinant was expressed with variable heterogeneity by invasive tumor cells in all individuals studied regardless of secretor status, but not in normal urothelium except for occassional umbrella cells. The Le$^y$ antigen showed increased expression or neosynthesis in invasive tumor cells of nonsecretors. In secretors, Le$^y$ antigen was expressed similarly in the invasive tumor cells but found in the normal urothelium also. Our studies are performed on formalin-fixed paraffin-embedded tissues, but as deparaffinization has been reported to alter antigenic expression, we have reexamined this question in comparative analyses of frozen and deparaffinized tissue sections of normal kidney/urothelium and normal colonic mucosa/colonic carcinoma. We did not observe a loss of antigen expression in formalin-fixed paraffin-embedded sections in comparison with frozen sections. In the present study we also compared the immunophenotypes of bladder tumor and normal urothelium of five cases in frozen and paraffin-embedded tissue sections side by side, and found no differences. Thus, it is likely that the determinants recognized by the present panel of antibodies reside on glycoproteins. Moreover, since the present study analyzes normal adjacent versus tumor cells in the same specimens from the same individuals processed in the same way, we can also correlate antibody reaction in tumor cells with the normal epithelial counterpart of the specimen in each case. The known normal phenotypes of RBC and epithelial cells serve as internal controls for our analysis.

It has also been reported that patients treated with radiotherapy had strong RCA-positive tests for ABH isoantigens, while untreated patients showed no reaction with the RCA test. However, four patients who were studied by us had received radiotherapy and all retained distinct phenotypes as described when normal urothelium, CIS, and invasive carcinoma were compared using the immunoperoxidase technique. Endothelial cells, erythrocytes, and normal urothelium served as internal controls for our analysis.

Previous investigators have emphasized that loss of ABH antigen expression is correlated with malignant change. We show that this is not a uniform feature of urothelial carcinomas, depending on the blood type and secretor status of the patient. It appears that there is a combination of changes in the various blood group specificities rather than a single change during malignant transformation, and that these vary depending on normal phenotype on the individual. Loss of A or B antigens and gain of H and $Le^x$ specificities was noted in A and B secretor individuals. In O secretors, there was loss of H antigen and gain in $Le^x$ determinant expression. Down-regulation of $Le^a$ was observed on tumor cells of O individuals. Expression of $Le^b$ on tumor cells of a $Le^{a-b-}$ RBC-typed individual was also noted. In nonsecretors there was gain or enhancement in $Le^y$ expression. In all individuals, uniform or heterogeneous expression of $Le^x$ antigen, not evident in normal urothelium, was highly characteristic of tumor cells. Also, expression of type 1 precursor determinant was preferentially seen in invasive bladder tumor cells and not in areas of CIS. Thus, it seems possible that enhanced expression of $Le^x$ antigen, accompanied by one or more changes in other blood group antigens, outlined above, could be reliable indicators of malignant transformation in bladder urothelium. A panel of well-characterized reagents to blood group-related antigens could be extremely useful in the immunopathological analysis of bladder tumors, particularly when the secretor status of the patient is known.

IV. BLADDER TUMORS

The 89 barbotage specimens from bladder tumor patients consisted of 14 patients with papilloma, 13 with CIS, 49 with transitional cell carcinoma (TCC) and 13 with positive cytology but negative cystoscopic examination and/or biopsy.

All immunocytology specimens were examined and interpreted without knowledge of clinical, histologic or cytologic findings. Granulocytes and superficial umbrella cells were excluded from analysis. Specimens containing more than rare urothelial cells showing $Le^x$ reactivity in cytoplasm or cell surface were considered positive.

Of the 89 bladder tumor specimens, 76 (85.4%) were $Le^x$ positive, while 55 (61.2%) had positive cytology and 12 (13.5%) had suspicious cytology (Table 1). Twelve of 14 (85.7%) specimens from patients with papilloma were $Le^x$ positive, while only one (7.1%) had positive cytology and two (14.2%) had suspicious cytology. Ten of 13 (76.9%) specimens from patients with CIS were $Le^x$ positive, while 9 (69.2%) had positive cytology and 3 (23.1%) had suspicious cytology. Nine of the 13 (69.2%) specimens from patients with positive cytology but negative cystoscopy and/or biopsy were $Le^x$ positive. Of the 49 patients with biopsy proven TCC, 45 (91.8%) were $Le^x$ positive while 32 (65.3%) had positive cytology and 7 (14.3%) had a suspicious cytology (Table 14).

The combination of either positive cytology and/or positive $Le^x$ resulted in an overall sensitivity of 93.2% (83/89). The corresponding sensitivities using the combined modalities for each of the bladder tumor groups were as follows: papilloma-85.7%; CIS-92.3%; and TCC-93.9% (Table 1).

Of the 40 control specimens obtained from patients with no history of bladder tumors, 34 were $Le^x$ negative. Five of the six false positive specimens were from patients with biopsy proven adenocarcinoma of the prostate, and the sixth was from a woman with widespread metastatic breast cancer. All 4 patients with BPH had $Le^x$ negative barbotage specimens while 5 of 8 specimens from prostate cancer patients were positive (Table 15). These results yield an overall specificity of 85% (34/40 true negatives) and, if prostate cancer patients are excluded, a specificity of 96.3% (31/32).

DISCUSSION

A vigorous barbotage yields the most representative sample of urothelial cells from the bladder and a number of techniques have evolved to identify the presence of malignant cells in those specimens. The most well established is the light microscopic examination of Papanicolaou stained smears of the urinary sediment. More recently, flow cytometry has been used, quite effectively, to identify carcinoma of the bladder by the presence of cells with abnormal DNA content. A new technique is now emerging based on the identification of tumor cells by alterations in expression of cell surface antigens. The present study deals within this last technique.

Neoplastic transformation of urothelial cells is associated with changes in the carbohydrate composition of membrane glycoproteins and glycolipids. Suppression of normally active glycosyltransferase can result in the deletion of antigens that are normally expressed. Although there is a very extensive literature addressing ABH antigen deletion in malignant and premalignant urothelium and the potential biological implications of such changes, the recent observation by Cordon-Cardo et al. regarding the influence of the secretor status on the expression of ABH antigens in normal urothelium mandates a careful re-examination of earlier studies and their conclusions.

Conversely, increased synthesis or activation of glycosyltransferases in bladder tumors with little or no activity in normal urothelium can result in aberrant expression of oligosaccharides on the cytoplasmic membrane of tumor cells. Detection of these tumor-associated antigens would enhance our ability to identify tumor cells, since these cell surface alterations may precede the morphologic changes of malignancy. The $Le^x$ determinant appears to be one such tumor-associated antigen in urothelium.

An immunohistochemical analysis by Cordon-Cardo et al. showed the presence of $Le^x$ only on the luminal surface of some superficial umbrella cells in normal urothelium. In 19 cystectomy specimens resected for invasive bladder cancer, histologically normal urothelium was invariably $Le^x$ negative except for umbrella cells, while $Le^x$ was expressed in areas of CIS in 11/14 cases and in all 19 cases in areas of invasive TCC. An extension of this analysis showed $Le^x$ expression in 12 of 14 papillomas, tumors with little or no potential for invasion or metastasis.

Evaluation of Le$^x$ reactivity in cytologic preparations is relatively simple. In approximately 90% of cases the epithelial cells are either entirely unreactive or positive in greater than 25% of the epithelial cells. However, some hypocellular specimens exhibit only few reactive cells which can make interpretation difficult. The presence of acute inflammatory cells which express Le$^x$ in the sediment does not interfere with interpretation since these can be easily distinguished from epithelial cells. Umbrella cells are usually quite characteristic on cytologic preparations, having abundant cytoplasm, a smooth and convex cytoplasmic membrane and one or more nuclei. Infrequently, one may encounter cells which are difficult to characterize as umbrella cells or neoplastic cells and for this reason we have considered that a positive preparation should have at least 5 Le$^x$ positive cells excluding cells that are obviously umbrella cells.

Finding Le$^x$ positive cells in 5/8 patients with prostrate cancer prompted us to study the immunoreactivity in paraffin sections of prostatic adenocarcinoma. Preliminary data indicates that approximately 15% of these tumors have populations of Le$^x$ positive tumor cell and the ductal epithelium also shows some Le$^x$ immunoreactivity. Interpretation of Le$^x$ immunocytology in bladder washings from patients with a history of prostate cancer or in patients with a suspicious rectal examination should therefore be interpreted cautiously.

Le$^x$ positive cells were present in 85.4% of barbotage specimens taken from tumor bearing patients. This compared favorably with the 61.2% sensitivity rate exhibited by conventional cytology. Furthermore, by combining the two modalities, an overall sensitivity of 93.2% is achieved. It is particularly gratifying that neo-expression of Le$^x$ occurs in papilloma as well as carcinoma, since detection of low grade, noninvasive bladder tumors by cytology has been inconsistent and disappointing in most reported series.

Our results are similar to those obtained by Huland using monoclonal antibody 486 P 3/12 on bladder wash specimens. Although Huland has not fully characterized this antibody, it is possible that it may recognize an immunodeterminant structure shared by Le$^x$ or recognize the Le$^x$ antigen itself. Monoclonal antibody 486 P 3/12 is an IgM lambda isotype A that was present in 17/19 bladder tumors and was also found in some superficial umbrella cells and in granulocytes. Although Huland used a human urothelial cell line to immunize the mice it has been shown that the Le$^x$ is extremely immunogenic in mice, and in fact, many tumor-associated antigens are blood group related substances.

We conclude that immunocytological detection of the Le$^x$ antigen on exfoliated bladder epithelial cells is a relatively simple and reproducible technique which enhances the detection of urothelial tumor cells, particularly from low grade and low stage neoplasms.

TABLE 14

Sensitivity of bladder tumor detection in barbotage specimens using Le$^x$ immunocytology, cytology, and a combination of either a (+)Le$^x$ and/or a (+)cytology.

|  | (+)Le$^x$ | (+) CYTOLOGY | SUSPICIOUS CYTOLOGY | (+)Le$^x$ and/or (+)CYTOLOGY |
|---|---|---|---|---|
| PAPILLOMA n = 14 | 12 (85.7%) | 1 (7.1%) | 2 (14.2%) | 12 (85.7%) |
| CIS n = 13 | 10 (76.9%) | 9 (69.2%) | 3 (23.1) | 12 (92.3%) |
| TCC n = 49 | 45 (91.8%) | 32 (65.3%) | 7 (14.3%) | 46 (93.9%) |
| (+)CYTOLOGY n = 13 | 9 (69.2%) | 13 (100%) | — | 13 (100%) |
| OVERALL | 76 (85.4%) | 55 (61.2%) | 12 (13.5%) | 83 (93.2%) |

TABLE 15

Specificity of Le$^x$ immunocytology in barbotage specimens from patients without a history of bladder cancer.

|  | (−)Le$^x$ | SPECIFICITY |
|---|---|---|
| Controls n = 40 | 34 | 85% |
| Excluding prostate cancer patients n = 32 | 31 | 96.3% |

V. HUMAN GERM CELL TUMOR

Figure 7B:
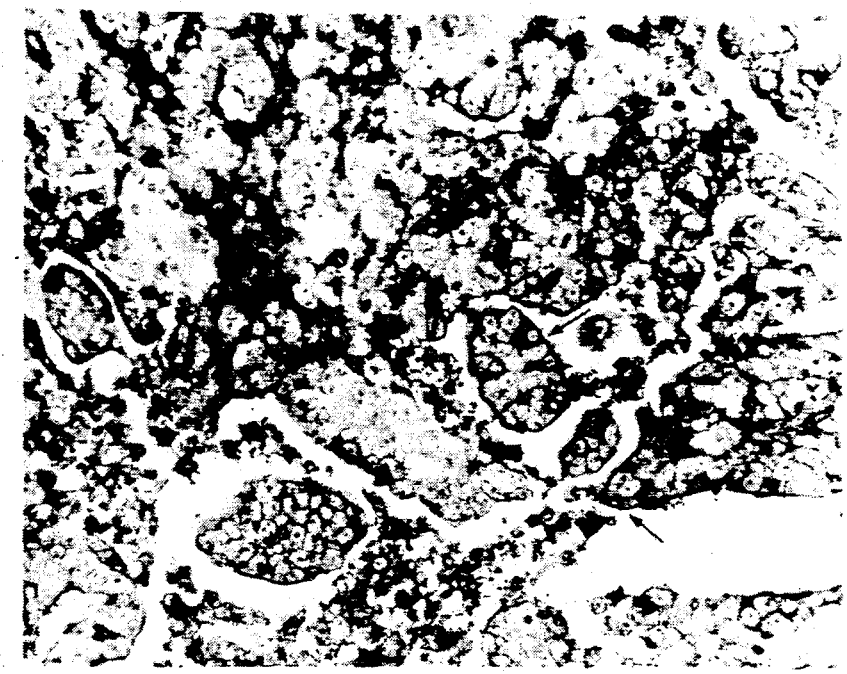
FIGS. 7A-B show the embryonal carcinoma from Patient 2 stained with hematoxylin and eosin (left) and with monoclonal antibody K-21 to precursor structure (right). Arrows: cytoplasmic membrane staining.
Figure 7A:
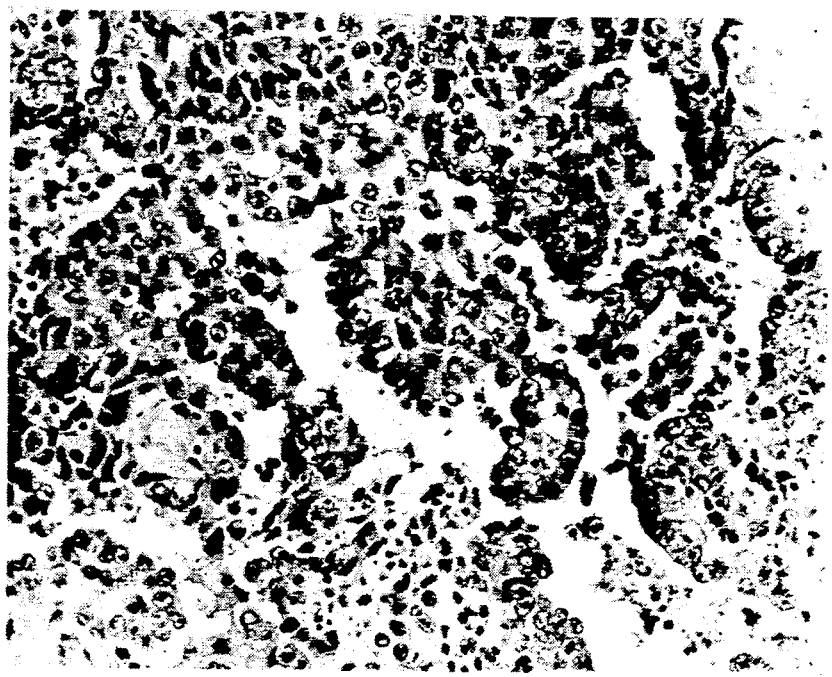
Figure 8B:
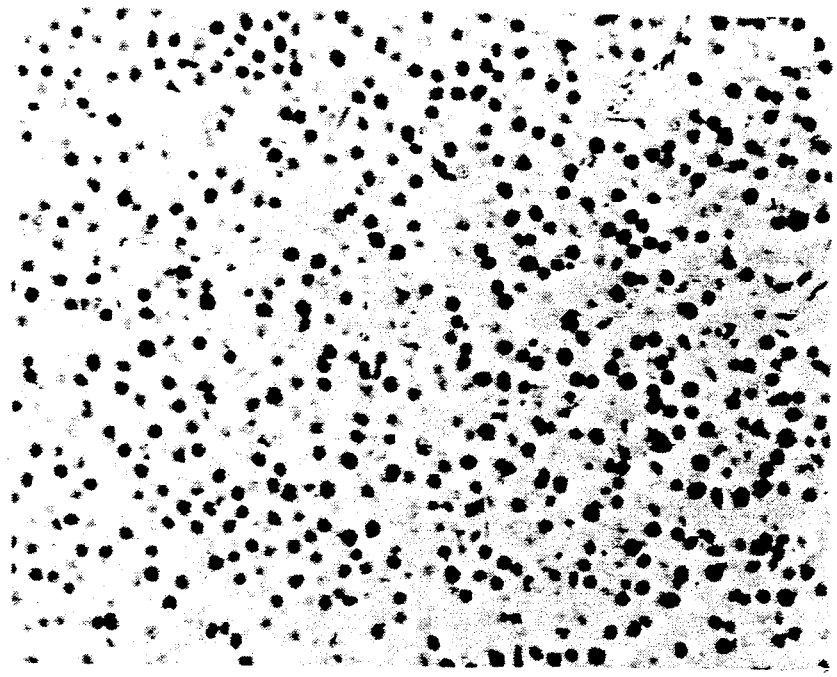
FIGS. 8A-8B show the seminoma from Patient 14 stained with hematoxylin and eosin (left) and with monoclonal antibody K-21 to precursor structure (right).
Figure 8A:
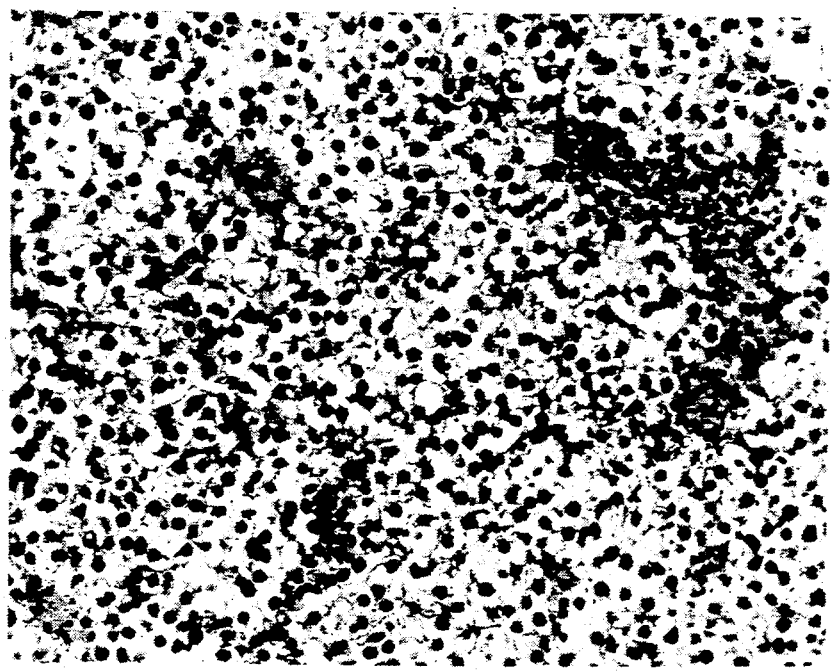

The tumors from Patients 1–5, 7, 8, and 10 were interpreted as embryonal carcinoma. Patients 11 and 13 had yolk sac tumor only in the tissue analyzed. Patients 14–28 had pure seminoma. The seminoma from Patients 14–22 had a classic morphology. In contrast, seminoma from Patients 23–28 has atypical features including increased mitotic index, nuclear pleomorphism and crowding, increased nuclearicytoplasmic ratio, promines nucleolus, and indistinct cytoplasmic membranes. Three patients had mixed GCT: Patient 9, embryonal carcinoma plus yolk sac tumor; Patient 12, yolk sac tumor plus seminoma (atypical). The morphologies of tumors from Patient 2 (embryonal carcinoma), Patient 14 (classical seminoma), and Patient 28 (seminoma with some atypical features) are deminostrated in FIGS. 7 (left), 8 (left), and 9 (left), respectively. The tumor of patient 29 could not conclusively be identified as a GCT. Thus, this patient was considered separately for analysis of immunoreactivity.

GCT Tumor Immunoreactivity

The distribution of blood group antigens in GCT is shown in relation to patient characteristics in Tables 16-A and 16-B. The immunophenotypic characterizations of the study cases are summarized in Table 17.

Precursor Type 1 Antigen. All of the embryonal carcinomas and yolk sac tumors uniformly expressed precursor structure, with the single exception of the tumor in Patient 12, which expressed the antigen in <50% of tumor cells. All of the classic seminomas (Patients 14–22), one atypical seminoma (Patient 24) and the seminomatous component of a mixed tumor (Patient 9) expressed no immunoreactivity for precursor antigen. Of the remaining atypical seminomas, two (Patients 25 and 27) has homogeneous expression of antigen, three (Patients 12, 23, and 28) expressed antigen in <50% of tumor cells and one (Patient 28) expressed antigen in only occasional tumor cells. Examples of immunoreactivity to K-21 monoclonal antibody are demonstrated for Patient 2 (embryonal carcinoma, K-21 positive), Patient 14 (seminoma, K-21 negative) and Patient 28 (seminoma, K-21 positive) in FIGS. 7 (right), 8 (right), and 9 (right), respectively.

H Antigen. Expression of H antigen was noted in the endothelial cells and erythrocytes of all specimens studies. Homogeneous tumor immunoreactivity was observed in 5 of 10 embryonal carcinomas and all yolk sac tumors except for Patient 12 in whom there was immunoreactivity in approximately 50% of tumor cells. Seminomas were nonreactive except for Patient 24 which expressed H antigen homogeneously and Patients 17 and 20 in which it was expressed in occasional cells.

A and B Antigens. A and B blood group antigen were present on erythrocytes and endothelial cells of corresponding blood type patients. Patients 2 and 11 expressed the appropriate blood group type A on tumor cells analyzed, embryonal carcinoma and yolk sac tumor, respectively. The other non-O blood type patients with embryonal carcinoma and yolk sac tumor (Patients 1, 3, 10, 12, and 13) had deletion of appropriate A or B blood type on tumor analyzed. Nine patients (Patients 12, 18-21, and 24-27) had deletion of appropriate A and/or B antigen in seminoma. No tumor studied had anomalous expression of these antigens or imcompatible immunophenotype for ABH isoantigens.

Lewis$^a$. Lewis$^a$ was expressed in 5 of 10 patients with embryonal carcinoma and 1 of 4 patients with yolk sac tumors. No expression in seminoma was noted.

Lewis$^b$. Immunoreactivity to Lewis$^b$ was present in 6 of 10 patients with embryonal carcinoma and 2 of 4 with yolk sac tumor. No patients with seminoma expressed Lewis$^b$ in tumor.

Lewis$^x$. X antigen was expressed in tumors of 2 of 4 patients with yolk sac histology. Two classic seminomas expressed X focally. No embryonal carcinoma had immunoreactivity for the X antigen.

Lewis$^y$. The tumors in 7 of 10 patients with embryonal carcinoma and 3 of 4 patients with yolk sac tumor expressed Y. For seminoma, 2 of 9 classic tumors and 3 of 7 with atypical morphological features expressed Y.

DISCUSSION

Blood group-related antigens are a group of cell surface carbohydrate structures which are present in the surface of RBC as well as many other nonerythroid cells. These antigens are formed by the sequential addition of sugar residues to precursor structures and their expression is modulated during development and maturation as well as neoplastic transformation. Andrews et al. demonstrated modulation of specific surface carbohydrate determinants, stage-specific embryonic antigens 1 and 3, during differentiation of closed human embryonal carinoma cells. Damjanov et al. also identified stage-specific embryonic antigen 3 in human embryonal carcinoma, yolk sac tumor, and teratoma but not in seminoma. Williams et al., Fukuda et al., and Rettig et al. demonstrated the presence of other carbohydrate determinants on the surface of embryonal carcinoma cells, including the epitope recognized by antibody K-21, a glycoprotein exhibiting specificity for blood group precursor type 1 chain. Finally, Teshima et al. showed marked differences in cell surface carbohydrates on germ cell tumor subtypes and commented on their potential use in establishing a more precise classification of these tumors.

We have used a panel of monoclonal antibodies and the lectin U. europaeus with specificities toward diverse blood group-related antigens to study human germ cell tumors. Type 1 precursor antigen as detected by K-21 antibody was present in all embryonal carcinomas and yolk sac tumors. In contrast, all classic seminomas were negative for K-21. Six of the seven atypical cases exhibited variable immunoreactivity with K-21. Thus, K-21 reactivity in seminoma appeared to correlate with atypical morphological features. The clinical significance of differing expression of precursor antigen in seminoma as determined by the monoclonal antibody K-21 remains to be defined and requires studying a larger number of patients. However, it is possible that the expression of K-21 in these tumors is an early marker of differentiation toward nonseminomatous histology.

Seminoma and nonseminomatous GCT differed in expression of the blood group antigen H. The majority of embryonal carcinomas and all yolk sac tumors studied expressed H. Only two classic seminomas and one atypical seminoma expressed immunoreactivity for the blood group antigen H. It is interesting that the two classic seminomas that expressed H also expressed Le$^x$ and Le$^y$ antigens (see Table 17, Patients 17 and 20). The higher proportion of H expression in yolk sac tumors compared to embryonal carcinoma may be a function of cellular differentiation since blood-forming elements are first produced in the fetal yolk sac.

Seminoma and nonseminomatous GCT (embryonal carcinoma and yolk sac tumor) differed in expression of the blood group antigens A, B, Le$^a$, Le$^b$, X, and Y. While embryonal carcinoma and yolk sac tumor had a distribution of expression, classic seminoma did not express these antigens with the two exceptions commented above. In addition, three atypical seminomas expressed variable amounts of Y antigen.

In conclusion, the monoclonal antibody K-21 detecting type 1 precursor antigen may be an important cell surface marker for GCT. All embryonal carcinomas and yolk sac tumors strongly expressed this antigen. This finding correlates with in vivo studies on teratocarcinoma by Rettig et al.. Seminoma, however, differs in expression of precursor antigen. The significance of heterogeneous expression in seminoma patients remains to be defined by studying a larger number of tumors which also may add insight into the histogenesis of GCT.

TABLE 16-A

Patient Characteristics
BLOOD GROUP ANTIGENS IN GCT

| Patient | Age | Blood type | Primary site | Tissue site |
|---|---|---|---|---|
| 1 | 25 | B | T$^a$ | T |
| 2 | 24 | A | T | T |
| 3 | 28 | A | T | T |
| 4 | 25 | O | T | T |
| 5 | 23 | O | T | T |
| 6 | 28 | O | T | T |
| 7 | 29 | O | T | T |
| 8 | 2 | O | T | T |
| 9 | 38 | O | T | T |
| 10 | 28 | AB | T | T |
| 11 | 18 | A | MED | MED |
| 12 | 27 | A | T | T |
| 13 | 27 | A | T | RP |
| 14 | 29 | O | T | T |
| 15 | 31 | O | T | T |

TABLE 16-A-continued
Patient Characteristics
BLOOD GROUP ANTIGENS IN GCT

| Patient | Age | Blood type | Primary site | Tissue site |
|---------|-----|------------|--------------|-------------|
| 16 | 30 | O | T | T |
| 17 | 32 | O | T | T |
| 18 | 22 | A | T | T |
| 19 | 32 | A | T | T |
| 20 | 32 | B | T | T |
| 21 | 50 | A | T | T |
| 22 | 21 | O | T | T |
| 23 | 36 | O | RP | RP |
| 24 | 29 | AB | T | T |
| 25 | 35 | A | T | T |
| 26 | 24 | A | RP | RP |
| 27 | 26 | AB | T | SCN |
| 28 | 28 | A | T | T |
| 29 | 20 | O | MED | AX.LN. |

<sup>a</sup>T, testis; RP, retroperitoneal; MED, mediastinum; SCN, supraclavicular lymph node; AX.LN., axillary lymph node; HCG, human chorionic gonadotropin level as measured in ng/ml; AFP, serum α-fetoprotein level as measured in ng/ml; LDH, serum lactate dehydrogenase level as measured in units/liter; EC, embryonic carcinoma; YS, yolk sac tumor; S, seminoma.

TABLE 16-B
Patient Characteristics
BLOOD GROUP ANTIGENS IN GCT

| Patient | Histology | Sites of metastases | Elevated pretreatment markers | |
|---------|-----------|---------------------|-------------------------------|---|
| 1 | EC | RP | HCG = | 25 |
| 2 | EC | Marker only | HCG = | 179 |
| 3 | EC | RP | HCG = | 9.3 |
|   |    |    | LDH = | 314 |
| 4 | EC | RP | LDH = | 476 |
|   |    | SCN |   |   |
| 5 | EC | RP | HCG = | 23,800 |
|   |    | Lung | LDH = | 849 |
| 6 | EC + YS | RP | HCG = | 56 |
|   |    | Lung | LDH = | 278 |
| 7 | EC | RP | LDH = | 675 |
| 8 | EC | RP | LDH = | 331 |
|   |    |    | HCG = | 2.1 |
| 9 | EC + S | RP | HCG = | 380 |
|   |    | Lung | AFP = | 634 |
|   |    | SCN | LDH = | 376 |
| 10 | EC | RP |   |   |
| 11 | YS | MED | AFP = | 10,360 |
|   |    |    | LDH = | 768 |
| 12 | YS + S | RP | HCG = | 125 |
|   |    |    | AFP = | 8,150 |
| 13 | YS | RP | AFP = | 8,150 |
| 14 | S | RP | HCG = | 20 |
|   |    |    | LDH = | 557 |
| 15 | S | None |   | None |
| 16 | S | RP | LDH = | 1,073 |
| 17 | S | None |   | None |
| 18 | S | None |   | None |
| 19 | S | None |   | None |
| 20 | S | None |   | None |
| 21 | S | None |   | None |
| 22 | S | RP | AFP = | 2,977 |
|   |    | Lung | LDH = | 930 |
| 23 | S | RP | HCG = | 9 |
|   |    |    | LDH = | 532 |
| 24 | S | RP | HCG = | 5 |
|   |    |    | LDH = | 343 |
| 25 | S | RP | LDH = | 3,680 |
|   |    | Lung |   |   |
| 26 | S | RP | LDH = | 794 |
| 27 | S | RP | HCG = | 57 |
|   |    | SCN | AFP = | 60 |
|   |    |    | LDH = | 825 |
| 28 | S | RP |   |   |
| 29 | Carcinoma | RP | AFP = | 560 |
|   |    | MED | LDH = | 14,460 |
|   |    | Marrow |   |   |

TABLE 17
Immunoreactivity of a panel of antibodies detecting blood group antigens in GCT

| Histology | Patient | PS | H | A | B | Le<sup>a</sup> | Le<sup>b</sup> | X | Y |
|-----------|---------|----|----|----|----|----|----|----|----|
| Embryonal carcinoma | 1 | X | ○ | ○ | ○ | — | — | X | X |
|  | 2 | X | X | — | ○ | X | X | ○ | — |
|  | 3 | X | X | ○ | ○ | X | — | ○ | X |
|  | 4 | X | ○ | ○ | ○ | — | — | ○ | ○ |
|  | 5 | X | X | ○ | ○ | ○ | ○ | ○ | ○ |
|  | 6 | X | X | ○ | ○ | X | X | ○ | — |
|  | 7 | X | X | ○ | ○ | ○ | ○ | ○ | — |
|  | 8 | X | ○ | ○ | ○ | ○ | ○ | ○ | — |
|  | 9 | X | ○ | ○ | ○ | ○ | ○ | ○ | ○ |
|  | 10 | X | ○ | ○ | ○ | — | — | ○ | X |
| Yolk sac | 11 | X | X | X | ○ | X | X | X | X |
|  | 12 | — | X | ○ | ○ | ○ | — | ○ | X |
|  | 6 | X | X | ○ | ○ | ○ | — | ○ | — |
|  | 13 | X | X | ○ | ○ | ○ | ○ | ○ | ○ |
| Classic seminoma | 14 | ○ | ○ | ○ | ○ | ○ | ○ | ○ | ○ |
|  | 15 | ○ | ○ | ○ | ○ | ○ | ○ | ○ | ○ |
|  | 16 | ○ | ○ | ○ | ○ | ○ | ○ | ○ | ○ |
|  | 17 | ○ | ○' | ○ | ○ | ○ | ○ | — | — |
|  | 18 | ○ | ○ | ○ | ○ | ○ | ○ | ○ | ○ |
|  | 19 | ○ | ○ | ○ | ○ | ○ | ○ | ○ | ○ |
|  | 20 | ○ | ○' | ○ | ○ | ○ | ○ | — | ○ |
|  | 21 | ○ | ○ | ○ | ○ | ○ | ○ | ○ | ○ |
|  | 22 | ○ | ○ | ○ | ○ | ○ | ○ | ○ | ○ |
|  | 9 | ○ | ○ | ○ | ○ | ○ | ○ | ○ | ○ |
| Atypical seminoma | 23 | — | ○ | ○ | ○ | ○ | ○ | ○ | ○ |
|  | 24 | ○ | X | ○ | ○ | ○ | ○ | ○ | X |
|  | 25 | X | ○ | ○ | ○ | ○ | ○ | ○ | ○ |
|  | 26 | ○' | ○ | ○ | ○ | ○ | ○ | ○ | ○ |
|  | 27 | X | ○ | ○ | ○ | ○ | ○ | ○ | — |
|  | 28 | — | ○ | ○ | ○ | ○ | ○ | ○ | ○ |
|  | 12 | X | ○ | ○ | ○ | ○ | ○ | ○ | ○ |
| Other | 29 | ○ | ○ | ○ | ○ | ○ | ○ | ○ | ○ |

PS, precursor structure, type 1 chain. Immunreactivities: X, homogeneous staining; —, <50% tumor cells positive; ○', occasional cells staining; ○, <50% tumor cells positive.

What is claimed is:

1. A method of distinguishing urothelial carcinoma from normal tissue which comprises obtaining a sample of biological tissue from a subject, contacting the tissue with a panel of monoclonal antibodies having specificities for A, B, Le<sup>a</sup>, Le<sup>b</sup>, Le<sup>x</sup>, Le<sup>y</sup>, or precursor type 1 chain antigens, and detecting the presence of A, B, Le<sup>a</sup>, Le<sup>b</sup>, Le<sup>x</sup>, Le<sup>y</sup>, or precursor type 1 chain antigens in the tissue by determining which antibodies form complexes, the presence of Le<sup>x</sup> antigen indicative of urothelial carcinoma, the presence of A and B antigen indicative of normal tissue, the presence of Le<sup>y</sup> antigen indicative of urothelial carcinoma in a nonsecretor, the presence of Le<sup>b</sup> and precursor type 1 chain antigen indicative of normal tissue in a secretor, and the presence of Le<sup>a</sup> antigen indicative of normal tissue in a nonsecretor.

2. The method of claim 1, wherein the panel comprises the monoclonal antibodies H 29-36 (ATCC No. HB 8248), S8 (ATCC No. HB 9036), T 174 (ATCC No. HB 8242), T 218 (ATCC No. HB 8249), P 12 (ATCC No. HB 8551), F 3 (ATCC No. HB 8217), and K 21 (ATCC No. HB 8549).

3. A method screening a human female subject for susceptibility to a urogenital infection which comprises determining whether the subject is a secretor by determining whether a biological fluid sample from the subject includes Lewis<sup>a</sup> or Lewis<sup>b</sup> antigens, by contacting the sample with a panel of monoclonal antibodies having specificities for Lewis<sup>a</sup> or Lewis<sup>b</sup> antigens, and determining which antibodies form complexes with the antigens in the sample, the formation of the Lewis<sup>a</sup> antigen/antibody complex indicating that the individual is a nonsecretor, the formation of the Lewis<sup>b</sup> antigen/antibody complex indicating that the individual is a secretor, and the presence of neither antigen/antibody complex indicating the secretor status of the subject is inconclusive, a nonsecretor being susceptible to a urogenital infection.

4. The method of claim 3, wherein the urogenital infection is a urinary infection.

5. The method of claim 3, wherein the urogenital infection is a genital infection.

6. The method of claim 3, wherein the urogenital infection is a vaginal epithelial infection.

7. The method of claim 3, wherein the urogenital infection is a kidney infection.

8. The method of claim 3, wherein the panel comprises the monoclonal antibodies T 174 (ATCC No. HB 8242) and T 218 (ATCC No. 8249).

9. A method of screening a human female subject for susceptibility to a urogenital infection which comprises determining whether the subject is a secretor by determining whether a biological fluid sample from the subject includes A, B or precursor type 1 chain antigens, by contacting the sample with a panel of monoclonal antibodies having specificities for A, B or precursor type 1 chain antigens, and ulux europeaus lectin, and determining which antibodies or lectin form complexes with the antigens in the sample, the formation of any such antigen/antibody complexe or antigen/lectin complexe indicating that the individual is a secretor, the lack of formation of any such antigen/antibody complexe or antigen/lectin complexe indicating that the subject is a nonsecretor, a nonsecretor being susceptible to a urogenital infection.

10. The method of claim 9, wherein the urogenital infection is a urinary infection.

11. The method of claim 9, wherein the urogenital infection is a genital infection.

12. The method of claim 9, wherein the urogenital infection is a vaginal epithelial infection.

13. The method of claim 9, wherein the urogenital infection is a kidney infection.

14. The method of claim 9, wherein the panel comprises the monoclonal antibodies H 29-36 (ATCC No. HB 8248), S8 (ATCC No. HB 9036), and K 21 (ATCC No. HB 8549).

* * * * *